(12) United States Patent
Poltaretskyi et al.

(10) Patent No.: US 12,357,389 B2
(45) Date of Patent: Jul. 15, 2025

(54) TARGETING TOOL FOR VIRTUAL SURGICAL GUIDANCE

(71) Applicant: Howmedica Osteonics Corp., Mahwah, NJ (US)

(72) Inventors: Sergii Poltaretskyi, Ependes (CH); Pascal Boileau, Nice (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 419 days.

(21) Appl. No.: 17/780,440

(22) PCT Filed: Nov. 20, 2020

(86) PCT No.: PCT/US2020/061585
§ 371 (c)(1),
(2) Date: May 26, 2022

(87) PCT Pub. No.: WO2021/113095
PCT Pub. Date: Jun. 10, 2021

(65) Prior Publication Data
US 2023/0000508 A1    Jan. 5, 2023

Related U.S. Application Data

(60) Provisional application No. 62/942,984, filed on Dec. 3, 2019.

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1703* (2013.01); *A61B 17/1778* (2016.11);
(Continued)

(58) Field of Classification Search
CPC ................ A61B 17/17; A61B 17/1703; A61B 17/1778; A61B 17/90; A61B 34/10; A61B 2034/107; A61B 2090/365
See application file for complete search history.

(56) References Cited

U.S. PATENT DOCUMENTS 9,498,233 B2 * 11/2016 Eash ..................... A61F 2/4609
2016/0209166 A1    7/2016 Larson, Jr. et al.
2018/0049622 A1    2/2018 Ryan et al.

FOREIGN PATENT DOCUMENTS

CH            664725 A5 *  3/1988
EP           3028661 A2    6/2016
WO  WO-2019245851 A1 * 12/2019 ........... A61B 17/142

OTHER PUBLICATIONS

International Preliminary Report on Patentability from International Application No. PCT/US2020/061585, dated Jun. 16, 2022, 10 pp.
(Continued)

*Primary Examiner* — Larry E Waggle, Jr.
(74) *Attorney, Agent, or Firm* — Shumaker & Sieffert, P.A.

(57) ABSTRACT

An example physical targeting tool includes a main body defining a channel configured to receive a tool, the channel having a longitudinal axis; a first physical targeting feature attached to the main body; and a second physical targeting feature attached to the main body, wherein the first physical targeting feature and the second physical targeting feature are displaced along the longitudinal axis of the channel.

19 Claims, 17 Drawing Sheets

(51) Int. Cl.
  *A61B 17/88* (2006.01)
  *A61B 90/00* (2016.01)
(52) U.S. Cl.
  CPC ..... *A61B 17/8897* (2013.01); *A61B 2034/107* (2016.02); *A61B 2090/365* (2016.02)

(56) References Cited

OTHER PUBLICATIONS

International Search Report and Written Opinion of International Application No. PCT/US2020/061585, dated Feb. 15, 2021, 14 pp.

* cited by examiner

TARGETING TOOL FOR VIRTUAL SURGICAL GUIDANCE

This application is a national stage application under 35 U.S.C. § 371 of PCT Application No. PCT/US2020/061585, filed Nov. 20, 2020, which claims the benefit of U.S. Provisional Application No. 62/942,984, filed Dec. 3, 2019. The entire contents of each of PCT Application No. PCT/US2020/061585, and U.S. Provisional Application No. 62/942,984 are incorporated herein by reference in their entirety.

BACKGROUND

Surgical joint repair procedures involve repair and/or replacement of a damaged or diseased joint. Many times, a surgical joint repair procedure, such as joint arthroplasty as an example, involves replacing the damaged joint with a prosthetic, or set of prosthetics, that is implanted into the patient's bone. To assist with positioning, the surgical procedure often involves the use of surgical instruments to control the shaping of the surface of the damaged bone and cutting or drilling of bone to accept the prosthetic.

SUMMARY

In some orthopedic surgical procedures, a surgeon may implant one or more implant devices in a patient. The surgeon may perform various surgical steps to prepare the patient's bone to receive the implant device. These surgical steps may include insertion of guide pins, modifications to a surface of the bone (e.g., via reaming), removal of portions of the bone (e.g., resection), creating anchorage points, or other surgical steps.

A visualization device may display virtual guidance that assists a surgeon in performing one or more of the surgical steps to prepare the patient's bone to receive the implant device. For instance, the visualization device may display a virtual axis to indicate a physical axis along which the surgeon is to position a rotating tool (e.g., a drill bit, a screw, a self-tapping guide pin, or other rotating tool) in order to perform a surgical step. The surgeon may achieve correct performance of the surgical step by aligning a shaft of the rotating tool with the displayed virtual axis, activating a driver of the rotating tool, and advancing the shaft of the rotating tool along the displayed virtual axis. However, in some scenarios, various tools used by the surgeon to perform the surgical step may obscure a portion of the virtual axis or otherwise interfere with the display of the virtual axis. For instance, from the surgeon's perspective, the driver of the rotating tool may obscure a portion of the virtual axis.

In accordance with one or more techniques of this disclosure, a visualization device may display virtual guidance that guides performance of a surgical step with the use of a physical targeting tool that attaches to a tool. The physical targeting tool may include a channel configured to receive a tool, and physical targeting features that are laterally offset from the channel. Where the tool is a rotating tool the channel may be configured to receive a shaft of the rotating tool. The visualization device may display the virtual guidance such that the surgeon may achieve correct performance of the surgical step by aligning one or more physical targeting features with the displayed virtual guidance. As the physical targeting features are laterally offset from the channel, the physical targeting features may not be obscured by the driver of the tool. Accordingly, the physical targeting features may aid the surgeon and can be a visible proxy to the actual channel. Moreover, virtual targeting features can be displayed relative to the physical targeting features, and virtual targeting features can be aligned with the physical targeting features so as to deliver non-obstructed views of such virtual targeting features. In this way, the techniques of this disclosure enable a surgeon to utilize tools, and associated drivers, to perform surgical steps with the assistance of virtual guidance.

The details of various examples of the disclosure are set forth in the accompanying drawings and the description below. Various features, objects, and advantages will be apparent from the description, drawings, and claims.

DETAILED DESCRIPTION

Figure 1:
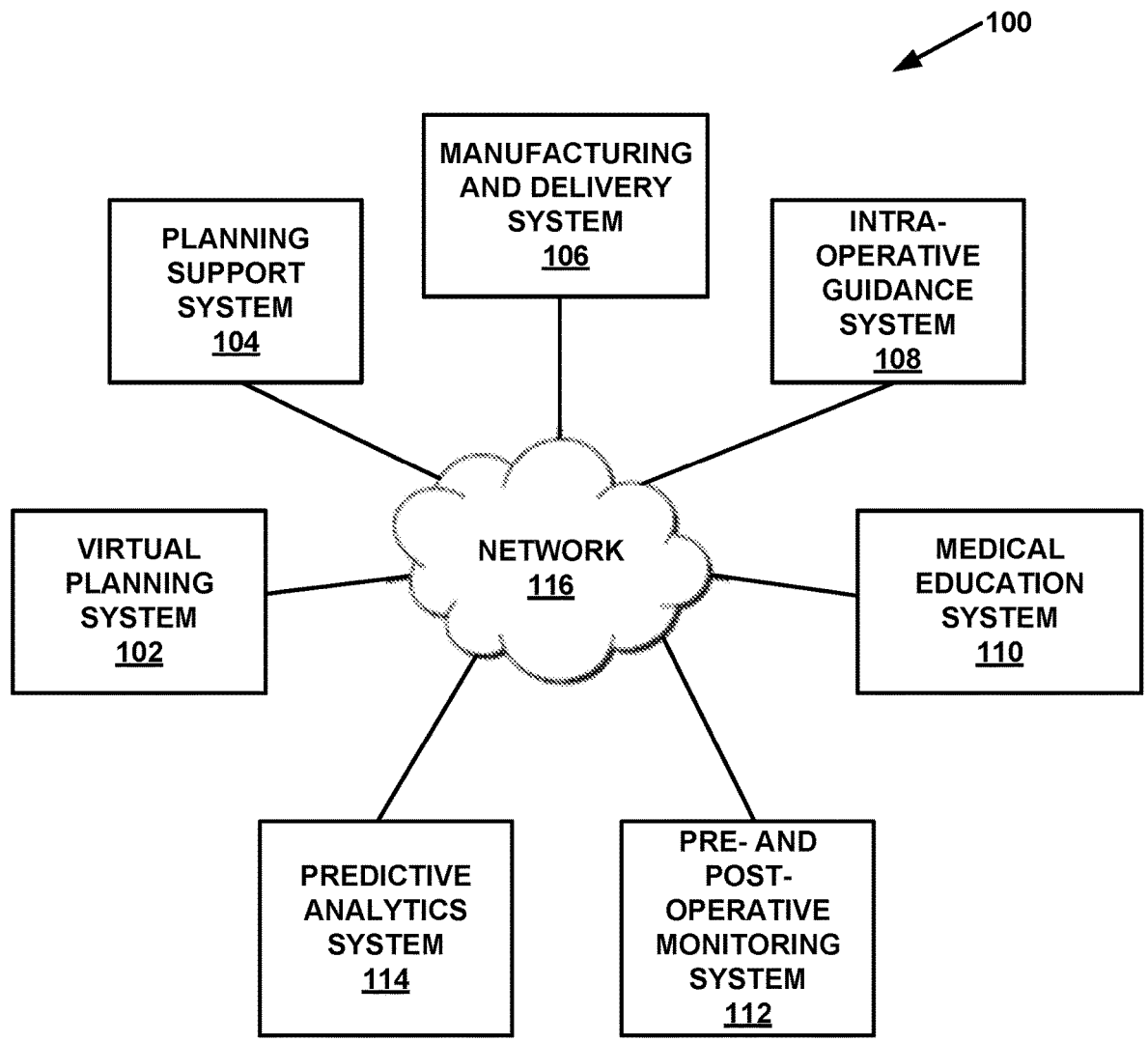
FIG. 1 is a block diagram of an orthopedic surgical system according to an example of this disclosure.

Orthopedic surgery can involve implanting one or more implant devices to repair or replace a patient's damaged or diseased joint. Virtual surgical planning tools that use image data of the diseased or damaged joint may be used to generate an accurate three-dimensional bone model that can be viewed and manipulated preoperatively by the surgeon. These tools can enhance surgical outcomes by allowing the surgeon to simulate the surgery, select or design an implant that more closely matches the contours of the patient's actual bone, and select or design surgical instruments and guide tools that are adapted specifically for repairing the bone of a particular patient. Use of these planning tools typically results in generation of a preoperative surgical plan, complete with an implant and surgical instruments that are selected or manufactured for the individual patient.

A surgeon may want to view details of the preoperative surgical plan relative to the patient's real bone during the actual procedure in order to more efficiently and accurately position and orient the implant components. For example, the surgeon may want to obtain intraoperative visualization that provides guidance for positioning and orientation of implant components, guidance for preparation of bone or tissue to receive the implant components, guidance for reviewing the details of a procedure or procedural step, and/or guidance for selection of tools or implants and tracking of surgical procedure workflow.

Accordingly, this disclosure describes systems and methods for using a mixed reality (MR) visualization system to assist with creation, implementation, verification, and/or modification of a surgical plan before and during a surgical procedure. Because MR may be used to interact with the surgical plan, this disclosure may also refer to the surgical plan as a "virtual" surgical plan. Visualization tools other than or in addition to mixed reality visualization systems may be used in accordance with techniques of this disclosure. A surgical plan, e.g., as generated by the BLUE-PRINT™ system, available from Wright Medical Group, N.V., or another surgical planning platform, may include information defining a variety of features of a surgical procedure, such as features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or tissue by the surgeon in bone or tissue preparation steps, and/or positions, axes, planes, angle and/or entry points defining placement of implant components by the surgeon relative to patient bone or tissue. Information such as dimensions, shapes, angles, surface contours, and/or orientations of anatomical features of the patient may be derived from imaging (e.g., x-ray, CT, MRI, ultrasound or other images), direct observation, or other techniques.

In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which they are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, hand-held, or otherwise viewable by a user. This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

The Microsoft HOLOLENS™ headset, available from Microsoft Corporation of Redmond, Washington, is an example of a MR device that includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as they exist in the real world. Video games set in imaginary worlds are a common example of VR. The term "VR" also encompasses scenarios where the user is presented with a fully artificial environment in which some virtual object's locations are based on the locations of corresponding physical objects as they relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

Visualization tools may utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Group, N.V. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitoring system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (i.e., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing systems configured to operate as a system. In some examples, one or more devices may be shared between two or more of the subsystems of orthopedic surgical system 100. For instance, in the previous examples, virtual planning system 102 and planning support system 104 may include the same server devices.

In the example of FIG. 1, the devices included in the subsystems of orthopedic surgical system 100 may communicate using communications network 116. Communications network 116 may include various types of communication networks including one or more wide-area networks, such as the Internet, local area networks, and so on. In some examples, communications network 116 may include wired and/or wireless communication links.

Figure 2:
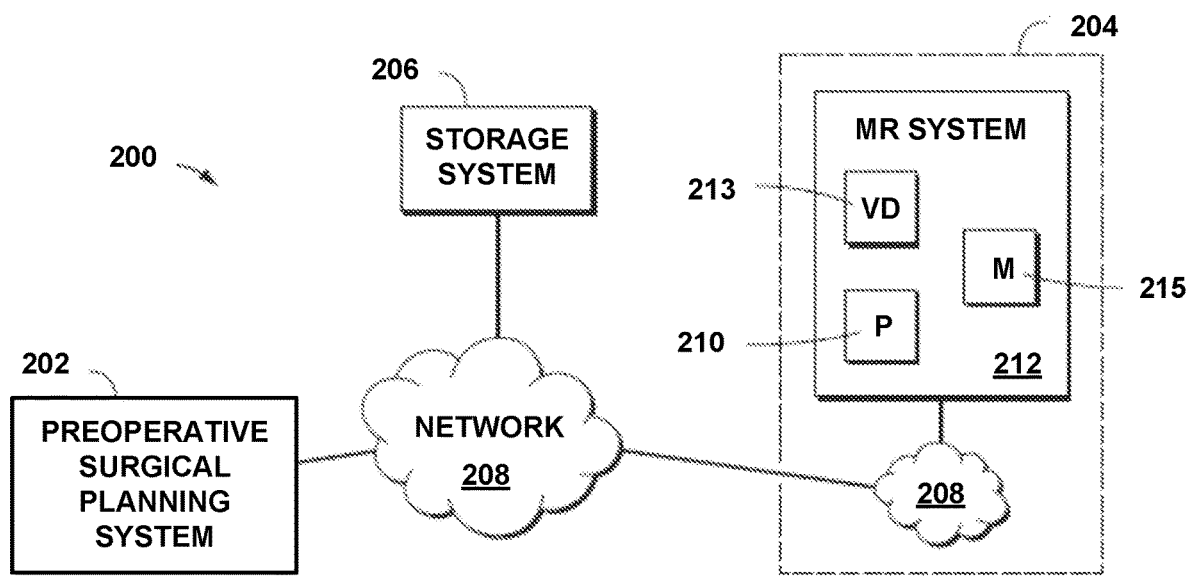
FIG. 2 is a block diagram of an orthopedic surgical system that includes a mixed reality (MR) system, according to an example of this disclosure.

Many variations of orthopedic surgical system 100 are possible in accordance with techniques of this disclosure. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206, and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities that will be described in further detail below. Processing device(s) 210 may also be referred to as processor(s). In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view. Different users may be located locally or remotely relative to one another, while interacting within MR system 212. If one or more users are remote, then those remote users may view similar virtual information to that of other local users while viewing different real-world views than the local users.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 to present virtual images, such as 3D virtual models, 2D images, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUEPRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans. For example, medical images of the patient's diseased or damaged bone typically are generated preoperatively in preparation for an orthopedic surgical procedure. The medical images can include images of the relevant bone(s) taken along the sagittal plane and the coronal plane of the patient's body. The medical images can include X-ray images, magnetic resonance imaging (MRI) images, computerized tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intraoperatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

In this way, FIG. 2 illustrates a surgical planning system that includes a preoperative surgical planning system 202 to generate a virtual surgical plan customized to repair an anatomy of interest of a particular patient. For example, the virtual surgical plan may include a plan for an orthopedic joint repair surgical procedure, such as one of a standard total shoulder arthroplasty or a reverse shoulder arthroplasty. In this example, details of the virtual surgical plan may include details relating to at least one of preparation of glenoid bone or preparation of humeral bone. In some examples, the orthopedic joint repair surgical procedure is one of a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, and an augmented glenoid reverse shoulder arthroplasty.

The virtual surgical plan may include a 3D virtual model corresponding to the anatomy of interest of the particular patient and a 3D model of a prosthetic component matched to the particular patient to repair the anatomy of interest or selected to repair the anatomy of interest. Furthermore, in the example of FIG. 2, the surgical planning system includes a storage system 206 to store data corresponding to the virtual surgical plan. The surgical planning system of FIG. 2 also includes MR system 212, which may comprise visualization device 213. In some examples, visualization device 213 is wearable by a user. In some examples, visualization device 213 is held by a user, or rests on a surface in a place accessible to the user. MR system 212 may be configured to present a user interface via visualization device 213. The user interface is visually perceptible to the user using visualization device 213. For instance, in one example, a screen of visualization device 213 may display real-world images and the user interface on a screen. In some examples, visualization device 213 may project virtual, holographic images onto see-through holographic lenses and also permit a user to see real-world objects of a real-world environment through the lenses. In other words, visualization device 213 may comprise one or more see-through holographic lenses and one or more display devices that present imagery to the user via the holographic lenses to present the user interface to the user.

In some examples, visualization device 213 is configured such that the user can manipulate the user interface (which is visually perceptible to the user when the user is wearing or otherwise using visualization device 213) to request and view details of the virtual surgical plan for the particular patient, including a 3D virtual model of the anatomy of interest (e.g., a 3D virtual bone of the anatomy of interest) and a 3D model of the prosthetic component selected to repair an anatomy of interest. In some such examples, visualization device 213 is configured such that the user can manipulate the user interface so that the user can view the virtual surgical plan intraoperatively, including (at least in some examples) the 3D virtual model of the anatomy of interest (e.g., a 3D virtual bone of the anatomy of interest). In some examples, MR system 212 can be operated in an augmented surgery mode in which the user can manipulate the user interface intraoperatively so that the user can visually perceive details of the virtual surgical plan projected in a real environment, e.g., on a real anatomy of interest of the particular patient. In this disclosure, the terms real and real world may be used in a similar manner. For example, MR system 212 may present one or more virtual objects that provide guidance for preparation of a bone surface and placement of a prosthetic implant on the bone surface. Visualization device 213 may present one or more virtual objects in a manner in which the virtual objects appear to be overlaid on an actual, real anatomical object of the patient, within a real-world environment, e.g., by displaying the virtual object(s) with actual, real-world patient anatomy viewed by the user through holographic lenses. For example, the virtual objects may be 3D virtual objects that appear to reside within the real-world environment with the actual, real anatomical object.

Figure 3:
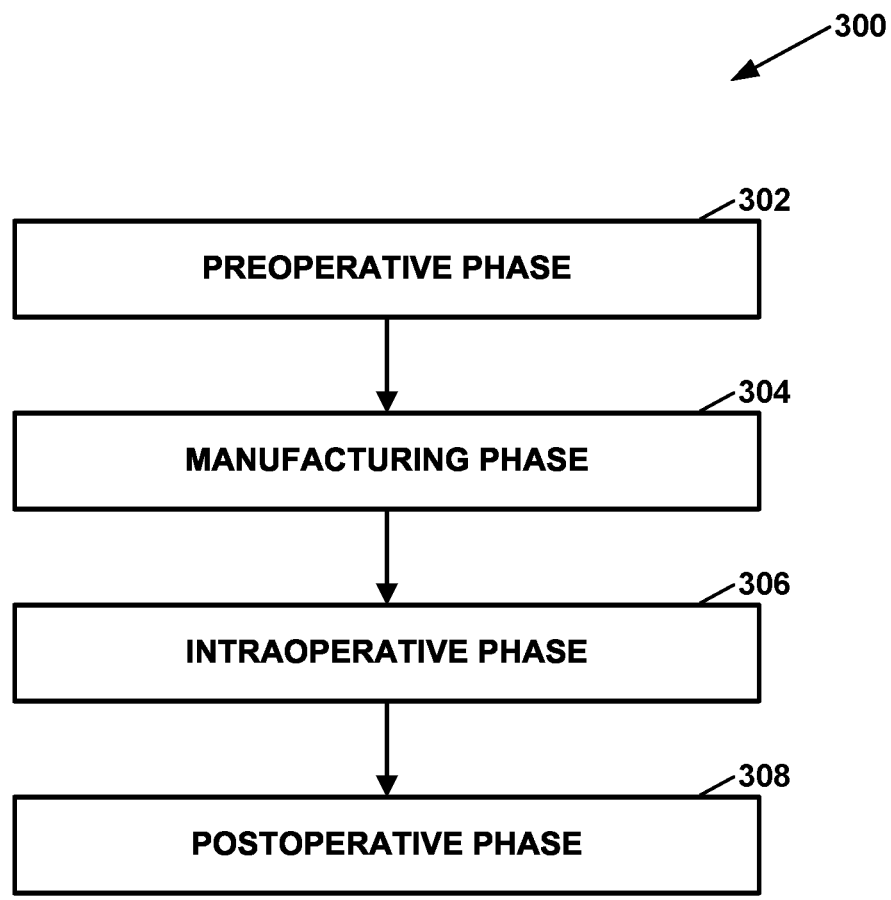
FIG. 3 is a flowchart illustrating example phases of a surgical lifecycle.

FIG. 3 is a flowchart illustrating example phases of a surgical lifecycle 300. In the example of FIG. 3, surgical lifecycle 300 begins with a preoperative phase (302). During the preoperative phase, a surgical plan is developed. The preoperative phase may be followed by a manufacturing and delivery phase (304). During the manufacturing and delivery phase, patient-specific items, such as parts and equipment, needed for executing the surgical plan are manufactured and delivered to a surgical site. For instance, a patient specific implant may be manufactured based on a design generated during the preoperative phase. An intraoperative phase follows the manufacturing and delivery phase (306). The surgical plan is executed during the intraoperative phase. In other words, one or more persons perform the surgery on the patient during the intraoperative phase. The intraoperative phase is followed by the postoperative phase (308). The postoperative phase includes activities occurring after the surgical plan is complete. For example, the patient may be monitored during the postoperative phase for complications.

As described in this disclosure, orthopedic surgical system 100 (FIG. 1) may be used in one or more of preoperative phase 302, the manufacturing and delivery phase 304, the intraoperative phase 306, and the postoperative phase 308. For example, virtual planning system 102 and planning support system 104 may be used in preoperative phase 302. Manufacturing and delivery system 106 may be used in the manufacturing and delivery phase 304. Intraoperative guidance system 108 may be used in intraoperative phase 306. Some of the systems of FIG. 1 may be used in multiple phases of FIG. 3. For example, medical education system 110 may be used in one or more of preoperative phase 302, intraoperative phase 306, and postoperative phase 308; pre- and postoperative monitoring system 112 may be used in preoperative phase 302 and postoperative phase 308. Predictive analytics system 114 may be used in preoperative phase 302 and postoperative phase 308.

Figure 4:
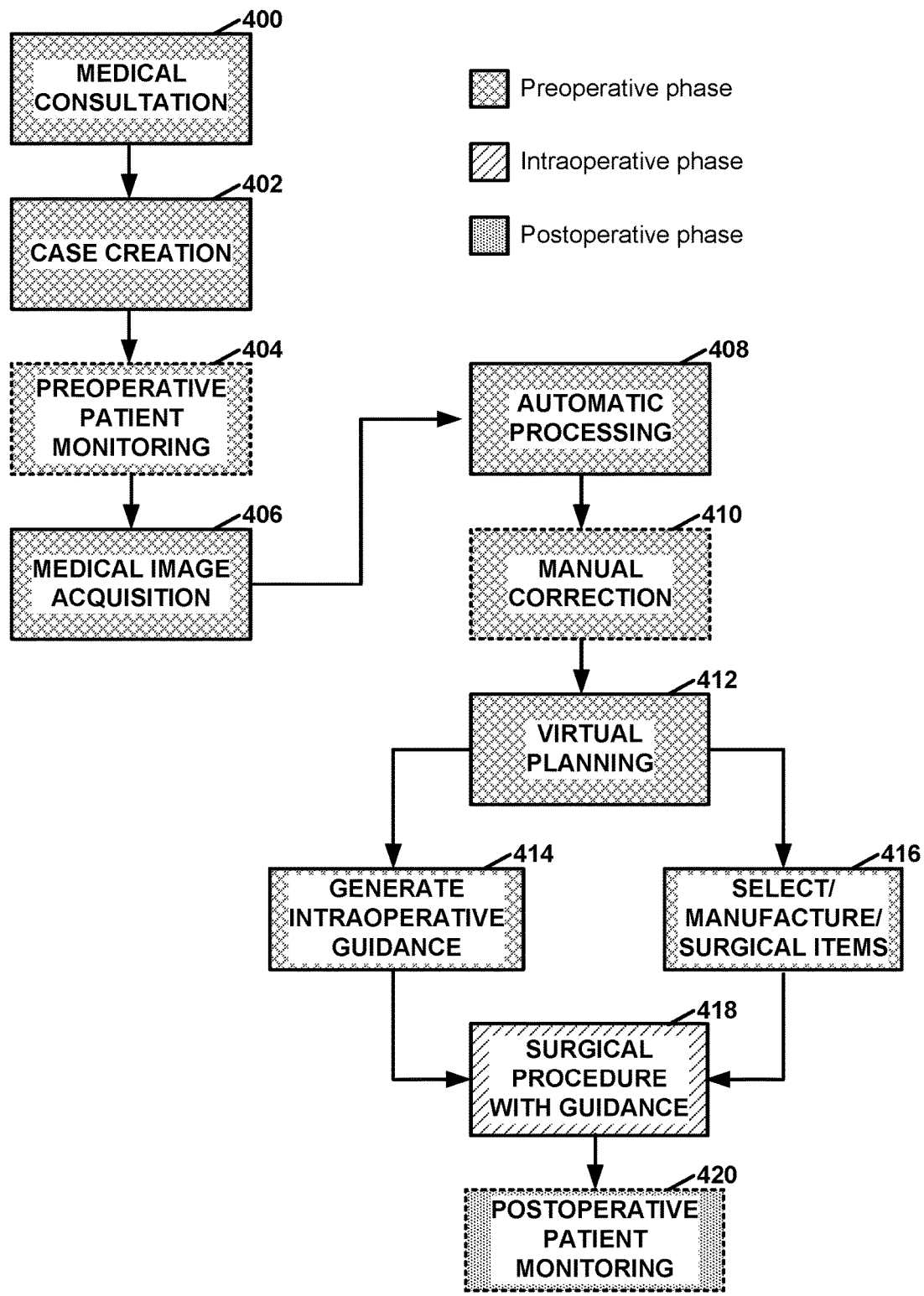
FIG. 4 is a flowchart illustrating preoperative, intraoperative and postoperative workflows in support of an orthopedic surgical procedure.

Various workflows may exist within the surgical process of FIG. 3. For example, different workflows within the surgical process of FIG. 3 may be appropriate for different types of surgeries. FIG. 4 is a flowchart illustrating preoperative, intraoperative and postoperative workflows in support of an orthopedic surgical procedure. In the example of FIG. 4, the surgical process begins with a medical consultation (400). During the medical consultation (400), a healthcare professional evaluates a medical condition of a patient. For instance, the healthcare professional may consult the patient with respect to the patient's symptoms. During the medical consultation (400), the healthcare professional may also discuss various treatment options with the patient. For instance, the healthcare professional may describe one or more different surgeries to address the patient's symptoms.

Furthermore, the example of FIG. 4 includes a case creation step (402). In other examples, the case creation step occurs before the medical consultation step. During the case creation step, the medical professional or other user establishes an electronic case file for the patient. The electronic case file for the patient may include information related to the patient, such as data regarding the patient's symptoms, patient range of motion observations, data regarding a surgical plan for the patient, medical images of the patients, notes regarding the patient, billing information regarding the patient, and so on.

The example of FIG. 4 includes a preoperative patient monitoring phase (404). During the preoperative patient monitoring phase, the patient's symptoms may be monitored. For example, the patient may be suffering from pain associated with arthritis in the patient's shoulder. In this example, the patient's symptoms may not yet rise to the level of requiring an arthroplasty to replace the patient's shoulder. However, arthritis typically worsens over time. Accordingly, the patient's symptoms may be monitored to determine whether the time has come to perform a surgery on the patient's shoulder. Observations from the preoperative patient monitoring phase may be stored in the electronic case file for the patient. In some examples, predictive analytics system 114 may be used to predict when the patient may need surgery, to predict a course of treatment to delay or avoid surgery or make other predictions with respect to the patient's health.

Additionally, in the example of FIG. 4, a medical image acquisition step occurs during the preoperative phase (406). During the image acquisition step, medical images of the patient are generated. The medical images may be generated in a variety of ways. For instance, the images may be generated using a Computed Tomography (CT) process, a Magnetic Resonance Imaging (MRI) process, an ultrasound process, or another imaging process. The medical images generated during the image acquisition step include images of an anatomy of interest of the patient. For instance, if the patient's symptoms involve the patient's shoulder, medical images of the patient's shoulder may be generated. The medical images may be added to the patient's electronic case file. Healthcare professionals may be able to use the medical images in one or more of the preoperative, intraoperative, and postoperative phases. In some examples, the medical images may be segmented into anatomical parts. For instance, medical images of the patient's shoulder may be segmented into a scapula, a humerus, etc. Three-dimensional (3D) models of the anatomical parts may be generated.

Furthermore, in the example of FIG. 4, an automatic processing step may occur (408). During the automatic processing step, virtual planning system 102 (FIG. 1) may automatically develop a preliminary surgical plan for the patient. In some examples of this disclosure, virtual planning system 102 may use machine learning techniques to develop the preliminary surgical plan based on information in the patient's virtual case file.

The example of FIG. 4 also includes a manual correction step (410). During the manual correction step, one or more human users may check and correct the determinations made during the automatic processing step. In some examples of this disclosure, one or more users may use mixed reality or virtual reality visualization devices during the manual correction step. In some examples, changes made during the manual correction step may be used as training data to refine the machine learning techniques applied by virtual planning system 102 during the automatic processing step.

A virtual planning step (412) may follow the manual correction step in FIG. 4. During the virtual planning step, a healthcare professional may develop a surgical plan for the patient. In some examples of this disclosure, one or more users may use mixed reality or virtual reality visualization devices during development of the surgical plan for the patient. As discussed in further detail below, during the virtual planning step, virtual planning system 102 may design a patient matched implant.

Furthermore, in the example of FIG. 4, intraoperative guidance may be generated (414). The intraoperative guidance may include guidance to a surgeon on how to execute the surgical plan. In some examples of this disclosure, virtual planning system 102 may generate at least part of the intraoperative guidance. In some examples, the surgeon or other user may contribute to the intraoperative guidance.

Additionally, in the example of FIG. 4, a step of selecting and manufacturing surgical items is performed (416). During the step of selecting and manufacturing surgical items, manufacturing and delivery system 106 (FIG. 1) may manufacture surgical items for use during the surgery described by the surgical plan. For example, the surgical items may include surgical implants (e.g., generic and/or patient specific), surgical tools, and other items required to perform the surgery described by the surgical plan.

In the example of FIG. 4, a surgical procedure may be performed with guidance from intraoperative system 108 (FIG. 1) (418). For example, a surgeon may perform the surgery while wearing a head-mounted MR visualization device of intraoperative system 108 that presents guidance information to the surgeon. The guidance information may help guide the surgeon through the surgery, providing guidance for various surgical steps in a surgical workflow, including sequence of surgical steps, details of individual surgical steps, and tool or implant selection, implant placement and position, and bone surface preparation for various surgical steps in the surgical procedure workflow.

Postoperative patient monitoring may occur after completion of the surgical procedure (420). During the postoperative patient monitoring step, healthcare outcomes of the patient may be monitored. Healthcare outcomes may include relief from symptoms, ranges of motion, complications, performance of implanted surgical items, and so on. Pre- and postoperative monitoring system 112 (FIG. 1) may assist in the postoperative patient monitoring step.

The medical consultation, case creation, preoperative patient monitoring, image acquisition, automatic processing, manual correction, and virtual planning steps of FIG. 4 are part of preoperative phase 302 of FIG. 3. The surgical procedures with guidance steps of FIG. 4 is part of intra-operative phase 306 of FIG. 3. The postoperative patient monitoring step of FIG. 4 is part of postoperative phase 308 of FIG. 3.

As mentioned above, one or more of the subsystems of orthopedic surgical system 100 may include one or more mixed reality (MR) systems, such as MR system 212 (FIG. 2). Each MR system may include a visualization device. For instance, in the example of FIG. 2, MR system 212 includes visualization device 213. In some examples, in addition to including a visualization device, an MR system may include external computing resources that support the operations of the visualization device. For instance, the visualization device of an MR system may be communicatively coupled to a computing device (e.g., a personal computer, backpack computer, smartphone, etc.) that provides the external computing resources. Alternatively, adequate computing resources may be provided on or within visualization device 213 to perform necessary functions of the visualization device.

Figure 5:
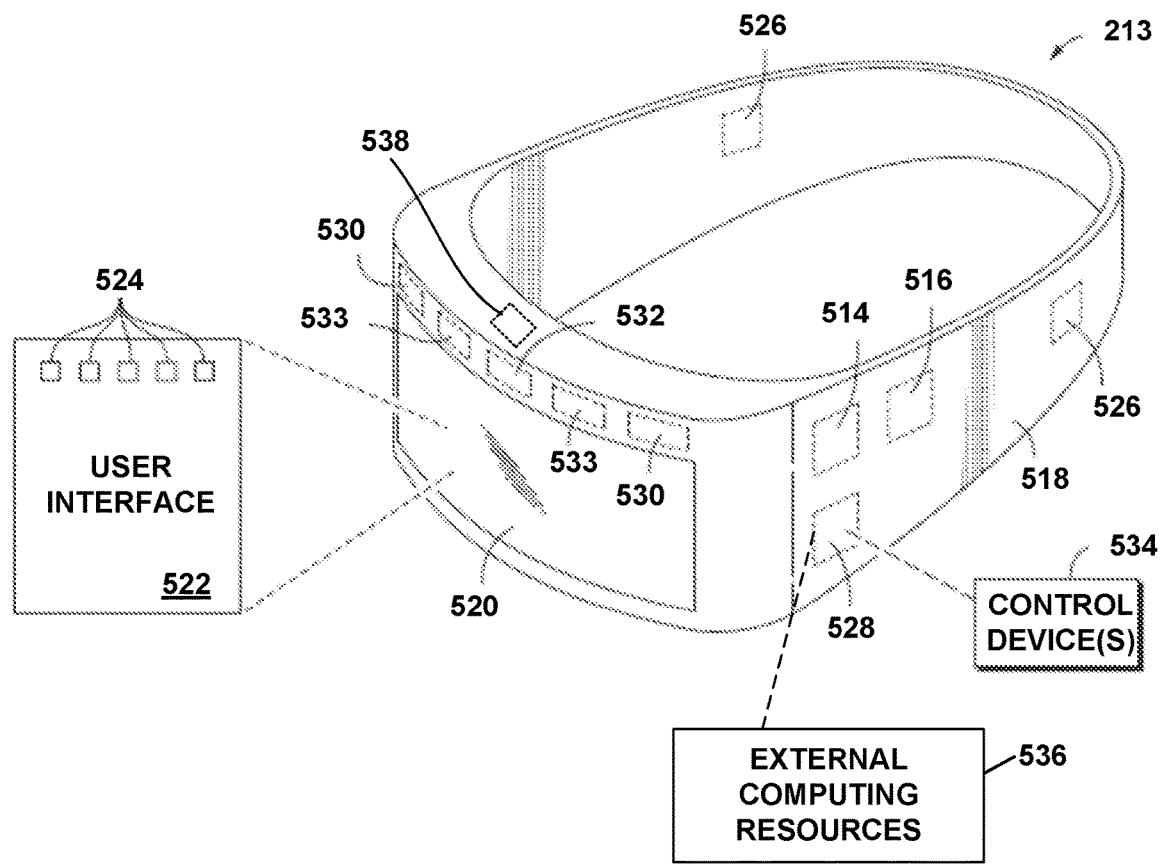
FIG. 5 is a schematic representation of a visualization device for use in a mixed reality (MR) system, according to an example of this disclosure.

FIG. 5 is a schematic representation of visualization device 213 for use in an MR system, such as MR system 212 of FIG. 2, according to an example of this disclosure. As shown in the example of FIG. 5, visualization device 213 can include a variety of electronic components found in a computing system, including one or more processor(s) 514 (e.g., microprocessors or other types of processing units) and memory 516 that may be mounted on or within a frame 518. Furthermore, in the example of FIG. 5, visualization device 213 may include a transparent screen 520 that is positioned at eye level when visualization device 213 is worn by a user. In some examples, screen 520 can include one or more liquid crystal displays (LCDs) or other types of display screens on which images are perceptible to a surgeon who is wearing or otherwise using visualization device 213 via screen 520. Other display examples include organic light emitting diode (OLED) displays. In some examples, visualization device 213 can operate to project 3D images onto the user's retinas using techniques known in the art.

In some examples, screen 520 includes see-through holographic lenses, sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 538 within visualization device 213. In other words, visualization device 213 may include one or more see-through holographic lenses to present virtual images to a user. Hence, in some examples, visualization device 213 can operate to project 3D images onto the user's retinas via screen 520, e.g., formed by holographic lenses. In this manner, visualization device 213 may be configured to present a 3D virtual image to a user within a real-world view observed through screen 520, e.g., such that the virtual image appears to form part of the real-world environment. In some examples, visualization device 213 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Although the example of FIG. 5 illustrates visualization device 213 as a head-wearable device, visualization device 213 may have other forms and form factors. For instance, in some examples, visualization device 213 may be a handheld smartphone or tablet.

Visualization device 213 can also generate a virtual user interface (UI) 522 that is visible to the user, e.g., as holographic imagery projected into see-through holographic lenses as described above. For example, UI 522 can include a variety of selectable virtual widgets 524 that allow the user to interact with a mixed reality (MR) system, such as MR system 212 of FIG. 2. Imagery presented by visualization device 213 may include, for example, one or more 3D virtual objects. Details of an example of UI 522 are described elsewhere in this disclosure. Visualization device 213 also can include a speaker or other sensory devices 526 that may be positioned adjacent the user's ears. Sensory devices 526 can convey audible information or other perceptible information (e.g., vibrations) to assist the user of visualization device 213.

Visualization device 213 can also include a transceiver 528 to connect visualization device 213 to a processing device 510 and/or to network 208 and/or to a computing cloud, such as via a wired communication protocol or a wireless protocol, e.g., Wi-Fi, Bluetooth, etc. Visualization device 213 also includes a variety of sensors to collect sensor data, such as one or more optical camera(s) 530 (or other optical sensors) and one or more depth camera(s) 532 (or other depth sensors), mounted to, on or within frame 518. In some examples, the optical sensor(s) 530 are operable to scan the geometry of the physical environment in which a user of MR system 212 is located (e.g., an operating room) and collect two-dimensional (2D) optical image data (either monochrome or color). Depth sensor(s) 532 are operable to provide 3D image data, such as by employing time of flight, stereo or other known or future-developed techniques for determining depth and thereby generating image data in three dimensions. Other sensors can include motion sensors 533 (e.g., Inertial Mass Unit (IMU) sensors, accelerometers, etc.) to assist with tracking movement.

MR system 212 processes the sensor data so that geometric, environmental, textural, or other types of landmarks (e.g., corners, edges or other lines, walls, floors, objects) in the user's environment or "scene" can be defined and movements within the scene can be detected. As an example, the various types of sensor data can be combined or fused so that the user of visualization device 213 can perceive 3D images that can be positioned, or fixed and/or moved within the scene. When a 3D image is fixed in the scene, the user can walk around the 3D image, view the 3D image from different perspectives, and manipulate the 3D image within the scene using hand gestures, voice commands, gaze line (or direction) and/or other control inputs. As another example, the sensor data can be processed so that the user can position a 3D virtual object (e.g., a bone model) on an observed physical object in the scene (e.g., a surface, the patient's real bone, etc.) and/or orient the 3D virtual object with other virtual images displayed in the scene. In some examples, the sensor data can be processed so that the user can position and fix a virtual representation of the surgical plan (or other widget, image or information) onto a surface, such as a wall of the operating room. Yet further, in some examples, the sensor data can be used to recognize surgical instruments and the position and/or location of those instruments.

Visualization device 213 may include one or more processors 514 and memory 516, e.g., within frame 518 of the visualization device. In some examples, one or more external computing resources 536 process and store information, such as sensor data, instead of or in addition to in-frame processor(s) 514 and memory 516. In this way, data processing and storage may be performed by one or more processors 514 and memory 516 within visualization device 213 and/or some of the processing and storage requirements may be offloaded from visualization device 213. Hence, in some examples, one or more processors that control the operation of visualization device 213 may be within visualization device 213, e.g., as processor(s) 514. Alternatively, in some examples, at least one of the processors that controls the operation of visualization device 213 may be external to visualization device 213, e.g., as processor(s) 210. Likewise, operation of visualization device 213 may, in some examples, be controlled in part by a combination one or more processors 514 within the visualization device and one or more processors 210 external to visualization device 213.

For instance, in some examples, when visualization device 213 is in the context of FIG. 2, processing of the sensor data can be performed by processing device(s) 210 in conjunction with memory or storage device(s) (M) 215. In some examples, processor(s) 514 and memory 516 mounted to frame 518 may provide sufficient computing resources to process the sensor data collected by cameras 530, 532 and motion sensors 533. In some examples, the sensor data can be processed using a Simultaneous Localization and Mapping (SLAM) algorithm, or other known or future-developed algorithms for processing and mapping 2D and 3D image data and tracking the position of visualization device 213 in the 3D scene. In some examples, image tracking may be performed using sensor processing and tracking functionality provided by the Microsoft HOLOLENS™ system, e.g., by one or more sensors and processors 514 within a visualization device 213 substantially conforming to the Microsoft HOLOLENS™ device or a similar mixed reality (MR) visualization device.

In some examples, MR system 212 can also include user-operated control device(s) 534 that allow the user to operate MR system 212, use MR system 212 in spectator mode (either as master or observer), interact with UI 522 and/or otherwise provide commands or requests to processing device(s) 210 or other systems connected to network 208. As examples, control device(s) 534 can include a microphone, a touch pad, a control panel, a motion sensor or other types of control input devices with which the user can interact.

Figure 6:
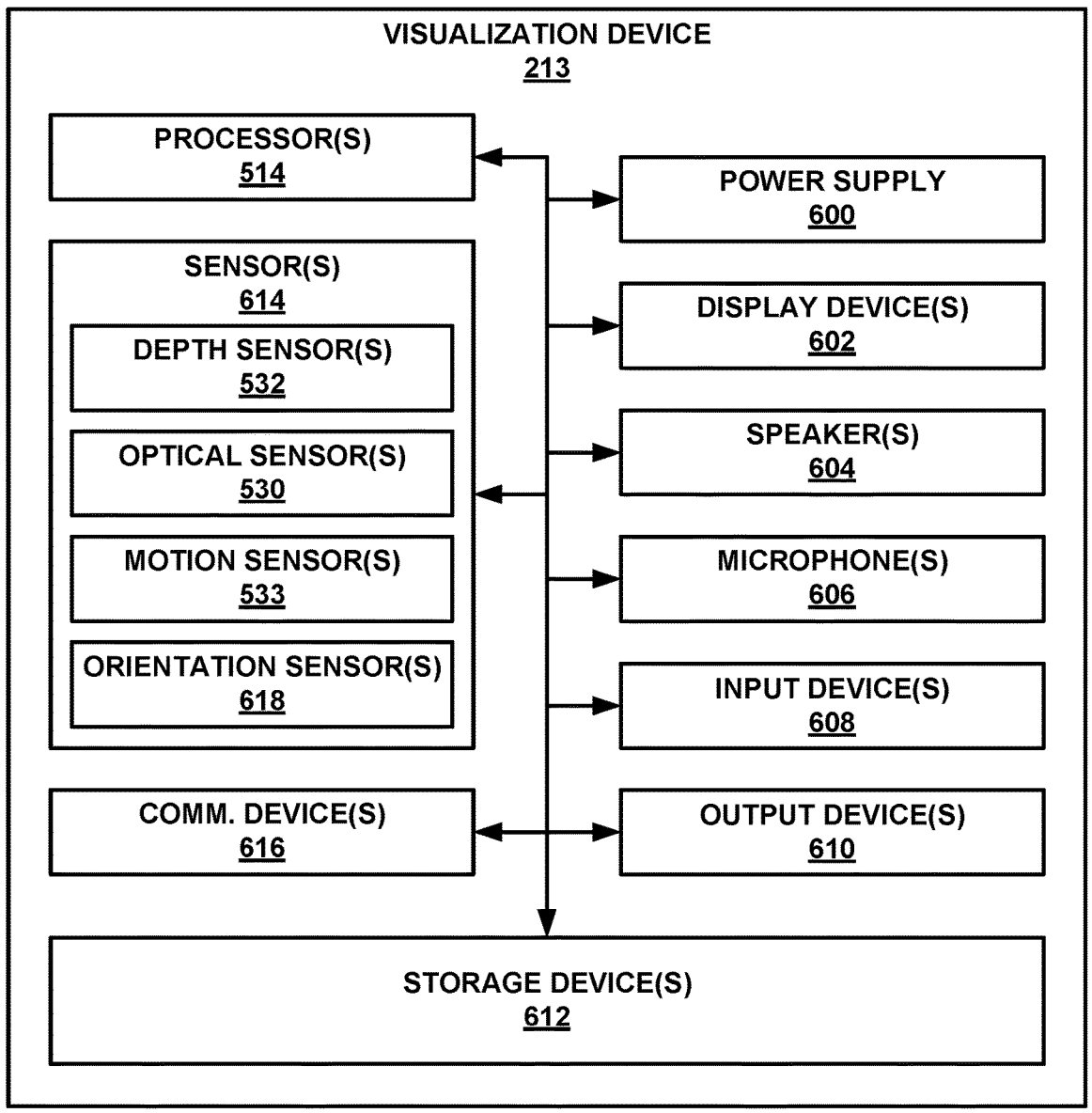
FIG. 6 is a block diagram illustrating example components of a visualization device for use in a mixed reality (MR) system, according to an example of this disclosure.

FIG. 6 is a block diagram illustrating example components of visualization device 213 for use in a MR system. In the example of FIG. 6, visualization device 213 includes processors 514, a power supply 600, display device(s) 602, speakers 604, microphone(s) 606, input device(s) 608, output device(s) 610, storage device(s) 612, sensor(s) 614, and communication devices 616. In the example of FIG. 6, sensor(s) 616 may include depth sensor(s) 532, optical sensor(s) 530, motion sensor(s) 533, and orientation sensor(s) 618. Optical sensor(s) 530 may include cameras, such as Red-Green-Blue (RGB) video cameras, infrared cameras, or other types of sensors that form images from light. Display device(s) 602 may display imagery to present a user interface to the user.

Speakers 604, in some examples, may form part of sensory devices 526 shown in FIG. 5. In some examples, display devices 602 may include screen 520 shown in FIG. 5. For example, as discussed with reference to FIG. 5, display device(s) 602 may include see-through holographic lenses, in combination with projectors, that permit a user to see real-world objects, in a real-world environment, through the lenses, and also see virtual 3D holographic imagery projected into the lenses and onto the user's retinas, e.g., by a holographic projection system. In this example, virtual 3D holographic objects may appear to be placed within the real-world environment. In some examples, display devices 602 include one or more display screens, such as LCD display screens, OLED display screens, and so on. The user interface may present virtual images of details of the virtual surgical plan for a particular patient.

In some examples, a user may interact with and control visualization device 213 in a variety of ways. For example, microphones 606, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, one or more cameras or other optical sensors 530 of sensors 614 may detect and interpret gestures (such as hand motions, hand gestures, finger motions, finger gestures, eye blinks, or other physical gestures) in order to perform operations as described above. As a further example, sensors 614 may sense gaze direction and perform various operations as described elsewhere in this disclosure. In some examples, input devices 608 may receive manual input from a user, e.g., via a handheld controller including one or more buttons, a keypad, a touchscreen, joystick, trackball, and/or other manual input media, and perform, in response to the manual user input, various operations as described above.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

A visualization system, such as MR system 212, may be configured to display virtual guidance including one or more virtual guides for performing work on a portion of a patient's anatomy. For instance, the visualization system may display virtual guidance that guides performance of a surgical step with the use of a physical targeting tool that attaches to the rotating tool. In some examples, a user such as a surgeon may view real-world objects in a real-world scene. The real-world scene may be in a real-world environment such as a surgical operating room. In this disclosure, the terms real and real-world may be used in a similar manner. The real-world objects viewed by the user in the real-world scene may include the patient's actual, real anatomy, such as an actual glenoid or humerus, exposed during surgery. The user may view the real-world objects via a see-through (e.g., transparent) screen, such as see-through holographic lenses, of a head-mounted MR visualization device, such as visualization device 213, and also see virtual guidance such as virtual MR objects that appear to be projected on the screen or within the real-world scene, such that the MR guidance object(s) appear to be part of the real-world scene, e.g., with the virtual objects appearing to the user to be integrated with the actual, real-world scene. For example, the virtual guidance may be projected on the screen of a MR visualization device, such as visualization device 213, such that the virtual guidance is overlaid on, and appears to be placed within, an actual, observed view of the patient's actual bone viewed by the surgeon through the transparent screen, e.g., through see-through holographic lenses. Hence, in this example, the virtual guidance may be a virtual 3D object that appears to be part of the real-world environment, along with actual, real-world objects.

A screen through which the surgeon views the actual, real anatomy and also observes the virtual objects, such as virtual anatomy and/or virtual surgical guidance, may include one or more see-through holographic lenses. The holographic lenses, sometimes referred to as "waveguides," may permit the user to view real-world objects through the lenses and display projected holographic objects for viewing by the user. As discussed above, an example of a suitable head-mounted MR device for visualization device 213 is the Microsoft HOLOLENS™ headset, available from Microsoft Corporation, of Redmond, Washington, USA. The HOLOLENS™ headset includes see-through, holographic lenses, also referred to as waveguides, in which projected images are presented to a user. The HOLOLENS™ headset also includes an internal computer, cameras and sensors, and a projection system to project the holographic content via the holographic lenses for viewing by the user. In general, the Microsoft HOLOLENS™ headset or a similar MR visualization device may include, as mentioned above, LCoS display devices that project images into holographic lenses, also referred to as waveguides, e.g., via optical components that couple light from the display devices to optical waveguides. The waveguides may permit a user to view a real-world scene through the waveguides while also viewing a 3D virtual image presented to the user via the waveguides. In some examples, the waveguides may be diffraction waveguides.

The visualization system (e.g., MR system 212/visualization device 213) may be configured to display different types of virtual guidance. Examples of virtual guidance include, but are not limited to, a virtual point, a virtual axis, a virtual angle, a virtual path, a virtual plane, virtual reticle, and a virtual surface or contour. As discussed above, the visualization system (e.g., MR system 212/visualization device 213) may enable a user to directly view the patient's anatomy via a lens by which the virtual guides are displayed, e.g., projected. The virtual guidance may guide or assist various aspects of the surgery. For instance, a virtual guide may guide at least one of preparation of anatomy for attachment of the prosthetic or attachment of the prosthetic to the anatomy.

The visualization system may obtain parameters for the virtual guides from a virtual surgical plan, such as the virtual surgical plan described herein. Example parameters for the virtual guides include, but are not necessarily limited to, guide location, guide orientation, guide type, guide color, etc.

The visualization system may display a virtual guide in a manner in which the virtual guide appears to be overlaid on an actual, real object, within a real-world environment, e.g., by displaying the virtual guide(s) with actual, real-world objects (e.g., at least a portion of the patient's anatomy) viewed by the user through holographic lenses. For example, the virtual guidance may be 3D virtual objects that appear to reside within the real-world environment with the actual, real object.

The techniques of this disclosure are described below with respect to a shoulder arthroplasty surgical procedure. Examples of shoulder arthroplasties include, but are not limited to, reversed arthroplasty, augmented reverse arthroplasty, standard total shoulder arthroplasty, augmented total shoulder arthroplasty, and hemiarthroplasty. However, the techniques are not so limited, and the visualization system may be used to provide virtual guidance information, including virtual guides in any type of surgical procedure. Other example procedures in which a visualization system, such as MR system 212, may be used to provide virtual guidance include, but are not limited to, other types of orthopedic surgeries; any type of procedure with the suffix "plasty," "stomy," "ectomy," "clasia," or "centesis,"; orthopedic surgeries for other joints, such as elbow, wrist, finger, hip, knee, ankle or toe, or any other orthopedic surgical procedure in which precision guidance is desirable. For instance, a visualization system may be used to provide virtual guidance for an ankle arthroplasty surgical procedure.

As discussed above, a MR system (e.g., MR system 212, MR system 1800A of FIG. 18, etc.) may receive a virtual surgical plan for attaching an implant to a patient and/or preparing bones, soft tissue or other anatomy of the patient to receive the implant. The virtual surgical plan may specify various surgical steps to be performed and various parameters for the surgical steps to be performed. As one example, the virtual surgical plan may specify a location on the patient's bone (e.g., glenoid, humerus, tibia, talus, etc.) for attachment of a guide pin. As another example, the virtual surgical plan may specify locations and/or orientations of one or more anchorage locations (e.g., screws, stems, pegs, keels, etc.).

Figure 7:
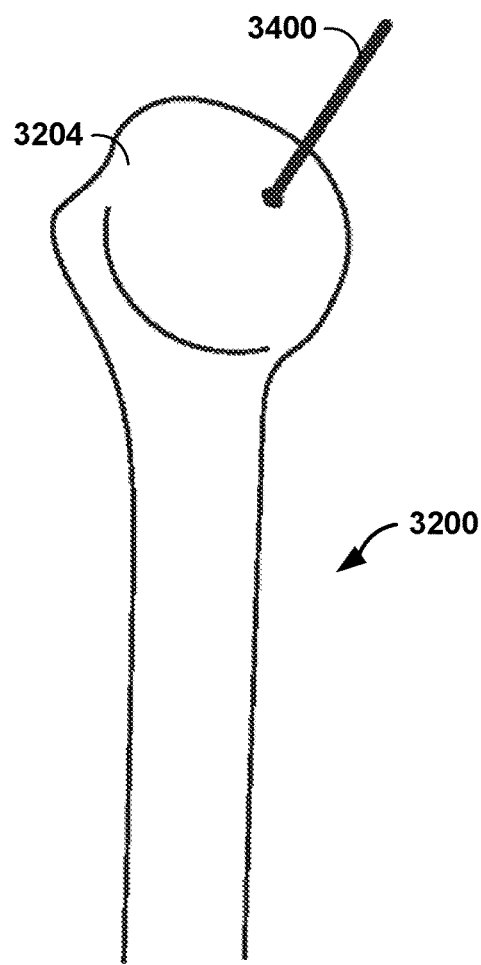
FIGS. 7 and 8 are conceptual diagrams illustrating an MR system providing virtual guidance for installation of a guide pin in a bone, in accordance with one or more techniques of this disclosure.
Figure 8:
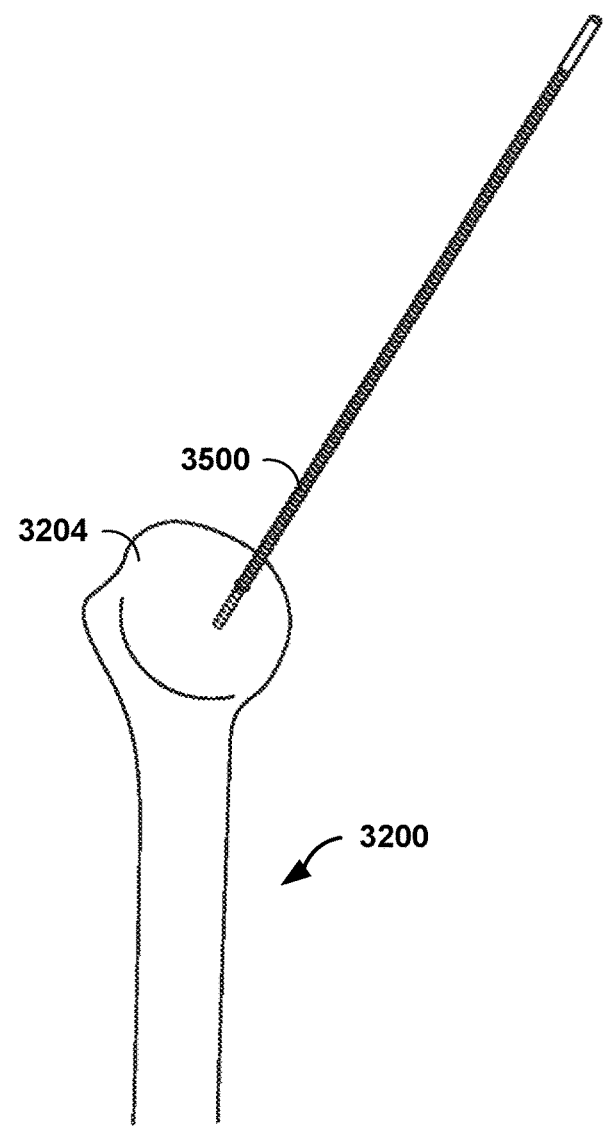

FIGS. 7 and 8 are conceptual diagrams illustrating an MR system providing virtual guidance for installation of a guide pin in a bone, in accordance with one or more techniques of this disclosure. In FIGS. 7 and 8 and other FIGS., for purposes of illustration, some of the surrounding tissue and some bone has been omitted for ease of illustration. As shown in FIG. 7, MR system 212 may display virtual axis 3400 on or relative to humeral head 3204 of humerus 3200. FIG. 7 and subsequent figures illustrate one example of what the surgeon, or other user, would see when viewing via visualization device 213. In particular, when viewing via visualization device 213 from the view shown in FIG. 7, the surgeon may see a portion of humerus 3200 and virtual axis 3400 (and/or other virtual guidance) overlaid on the portion of humerus 3200.

To display virtual axis 3400, MR system 212 may determine a location on a virtual model of humerus 3200 at which a guide is to be installed. MR system 212 may obtain the location from a virtual surgical plan (e.g., the virtual surgical plan described above as generated by virtual planning system 202). The location obtained by MR system 212 may specify one or both of coordinates of a point on the virtual model and a vector. The point may be the position at which the guide is to be installed and the vector may indicate the angle/slope at which the guide is to be installed. As such, MR system 212 may display a virtual drilling axis having parameters obtained from the virtual surgical plan, and the virtual drilling axis may be configured to guide drilling of one or more holes in the glenoid (e.g., for attachment of a guide pin to the scapula).

A virtual model of humerus 3200 may be registered with humerus 3200 such that coordinates on the virtual model approximately correspond to coordinates on humerus 3200. For instance, MR system 212 may generate a transformation matrix between the virtual model of humerus 3200 and an observed portion of humerus 3200. This transformation matrix may allow for translation along the x, y, and z axes of the virtual model and rotation about the x, y and z axes in order to achieve and maintain alignment between the virtual and observed bones. In some examples, after registration is complete, MR system 212 utilize the results of the registration to perform simultaneous localization and mapping (SLAM) (or any other tracking algorithm) to maintain alignment of the virtual model to the corresponding observed object. As such, by displaying virtual axis 3400 at the determined location on the virtual model, MR system 212 may display virtual axis 3400 at the planned position on humerus 3200.

The surgeon may attach a guide pin to humerus 3200 using the displayed virtual guidance. For instance, where the guide pin includes a self-tapping threaded distal tip, the surgeon may align the guide pin with the displayed virtual axis 3400 and utilize a drill or other instrument to install the guide pin in humerus 3200.

FIG. 8 is a conceptual diagram illustrating guide 3500 as installed in humeral head 3204. Guide 3500 may take the form of an elongated pin to be mounted in a hole formed in the humeral head. As shown in FIGS. 7 and 8, by displaying virtual axis 3400, a surgeon may install guide 3500 at the planned position on humeral head 3204.

As discussed above, FIG. 7 illustrates an example of what the surgeon, or other user, would see when viewing via visualization device 213 from the view shown in FIG. 7. In particular, FIG. 7 shows what the surgeon would see when the surgeon's gaze line is from a side view/substantially orthogonal to the axis of the surgical step being performed (e.g., virtual axis 3400). However, the surgeon is not likely to view the patient from such an angle when operating a driver of a rotating tool (e.g., a drill or motor that rotates the guide pin, a drill bit, a reamer, or the like). Instead, when operating the driver of the rotating tool, the surgeon is likely to view the patient from behind the drill or motor while operating the drill or motor, with a gaze line substantially parallel to an axis of the surgical step being performed.

Figure 9:
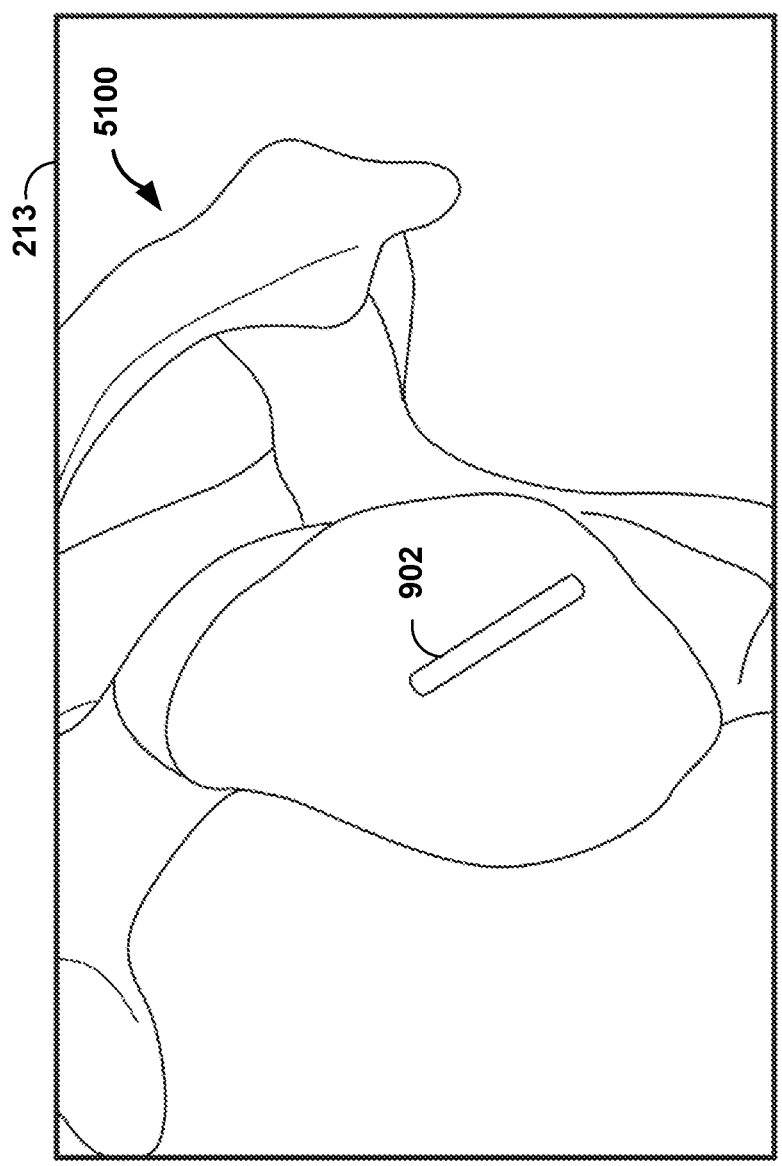
FIG. 9 is a conceptual diagram of virtual guidance that may be provided by an MR system.

FIG. 9 is a conceptual diagram of virtual guidance that may be provided by an MR system according to one or more examples of this disclosure. As shown in FIG. 9, a surgeon may view a portion of scapula 5100 through visualization device 213 with a gaze line substantially parallel (e.g., closer to parallel than perpendicular) to an axis of the surgical step being performed. For instance, as shown in FIG. 9 where visualization device 213 displays virtual axis 902 to guide use of a rotating tool to perform a surgical step on scapula 5100, the axis of the surgical step being performed may correspond to virtual axis 902. As such, the surgeon may view scapula 5100 through visualization device 213 with a gaze line substantially parallel to an axis of virtual axis 902.

As discussed above, in some examples, the surgeon may utilize one or more tools to perform work on portion of a patient's anatomy (e.g., scapula 5100, humerus 3200, etc.). For instance, the surgeon may utilize a driver to drive (e.g., provide rotational power to) a rotating tool. Examples of rotating tools include, but are not limited to, guide pins (e.g., self-tapping guide pins, such as guide 3500), reaming tools, drill bits, and screw drivers.

As also discussed above, MR system 212 may provide virtual guidance to assist the surgeon in performing surgical steps. For instance, as shown in FIG. 9, visualization device 213 of MR system 212 may display virtual axis 902 to guide use of a rotating tool to perform a surgical step on scapula 5100. The surgeon may achieve correct performance of the surgical step by aligning a shaft of the rotating tool with virtual axis 902, activating a driver of the rotating tool, and advancing the shaft of the rotating tool along the displayed virtual axis. However, in some scenarios, the rotating tool, the driver of the rotating tool, and/or various tools used by the surgeon may obscure or otherwise interfere with a portion of the virtual guidance being presented by visualization device 213.

Figure 10:
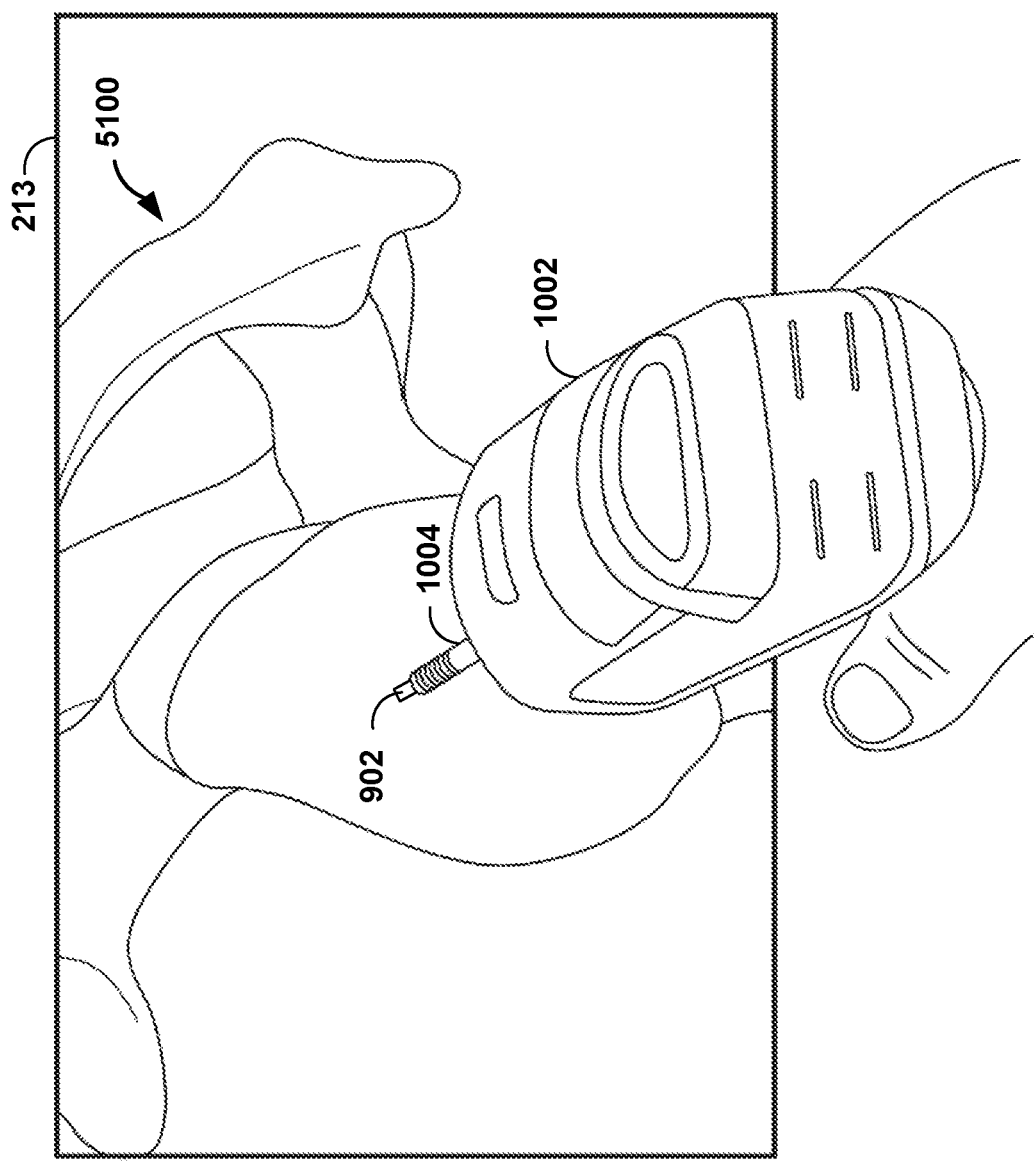
FIG. 10 is a conceptual diagram of tools obscuring a portion of virtual guidance provided by an MR system.

FIG. 10 is a conceptual diagram of tools obscuring a portion of virtual guidance provided by an MR system. As shown in FIG. 10, to utilize virtual axis 902, the surgeon may align a shaft of rotating tool 1004 with virtual axis view a portion of scapula 5100 through visualization device 213 with a gaze line substantially parallel (e.g., closer to parallel than perpendicular) to an axis of the surgical step being performed. As can be seen in FIG. 10, when viewing with a gaze line substantially parallel to the axis of the surgical step being performed (i.e., substantially parallel to virtual axis 902) driver 1002 obscures the displayed virtual guidance (i.e., virtual axis 902). With the virtual guidance obscured, it may be difficult for the surgeon to find and/or maintain alignment between a tool being used and the virtual guidance. For instance, it may be difficult for the surgeon to maintain alignment between a shaft of rotating tool 1004 and virtual axis 902.

In accordance with one or more techniques of this disclosure, MR system 212 may display virtual guidance that guides performance of a surgical step with the use of a physical targeting tool that attaches to a tool. Where the tool is a rotating tool, the physical targeting tool may include a channel through which the shaft of the rotating tool is inserted, and one or more physical targeting features that are offset from the channel. Further details of one example of a physical targeting tool are discussed below with reference to FIGS. 11A-11C. MR system 212 may display the virtual guidance such that the surgeon may achieve correct performance of the surgical step by aligning the one or more physical targeting features of the physical targeting tool with the displayed virtual guidance. As the physical targeting features are offset from the channel, the physical targeting features may not be obscured by the driver of the rotating tool. As such, MR system 212 may display virtual guidance to be aligned with the physical targeting features without the virtual guidance being obscured. In this way, the techniques of this disclosure enable a surgeon to utilize tools, and associated drivers, to perform surgical steps with the assistance of virtual guidance.

Figure 11A:
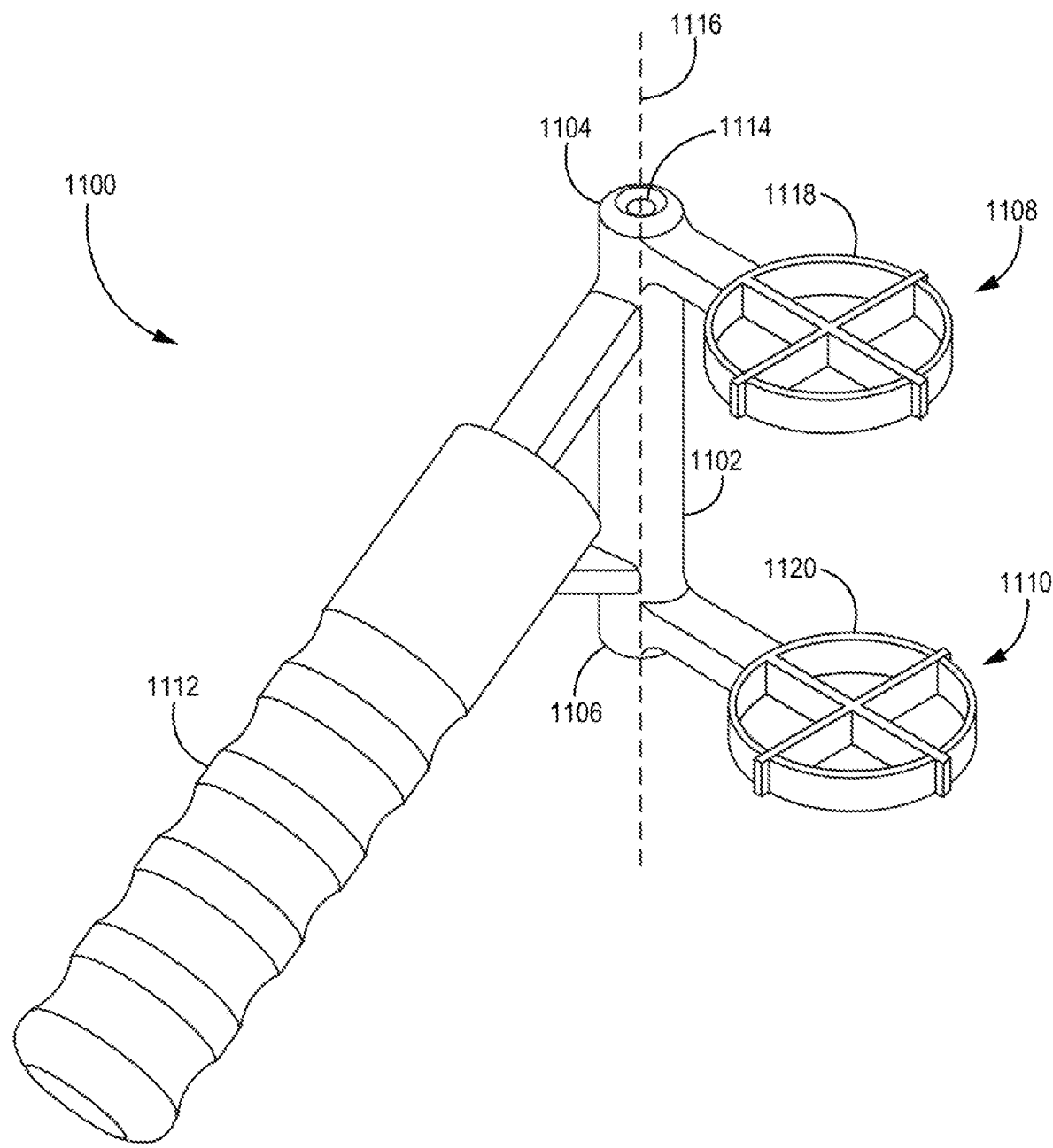
FIGS. 11A-11C illustrate various views of one example of a physical targeting tool, in accordance with one or more techniques of this disclosure.
Figure 11C:
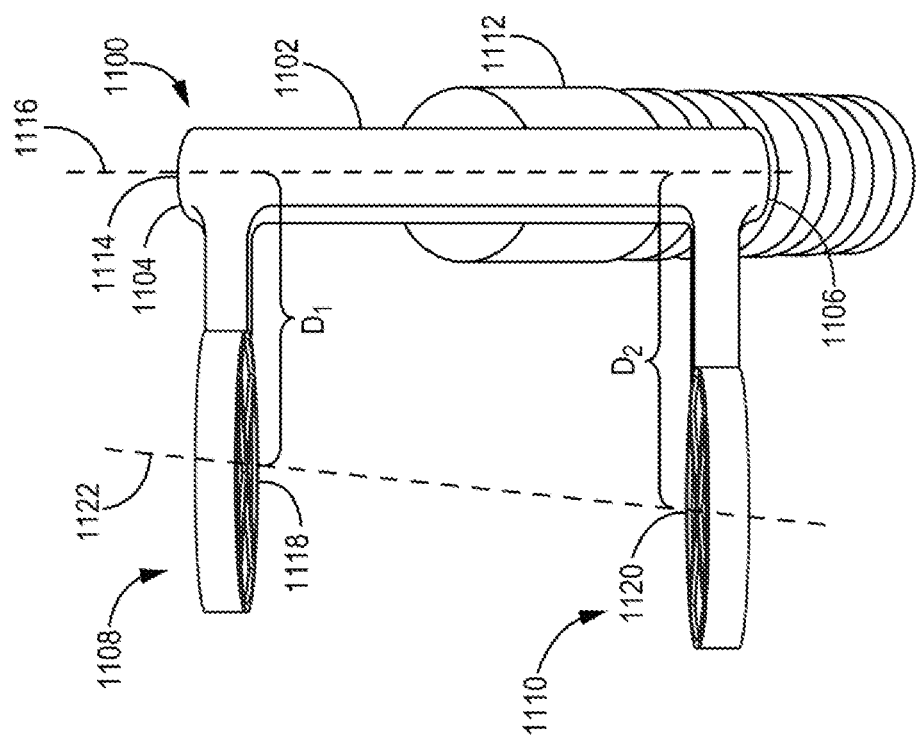
Figure 11B:
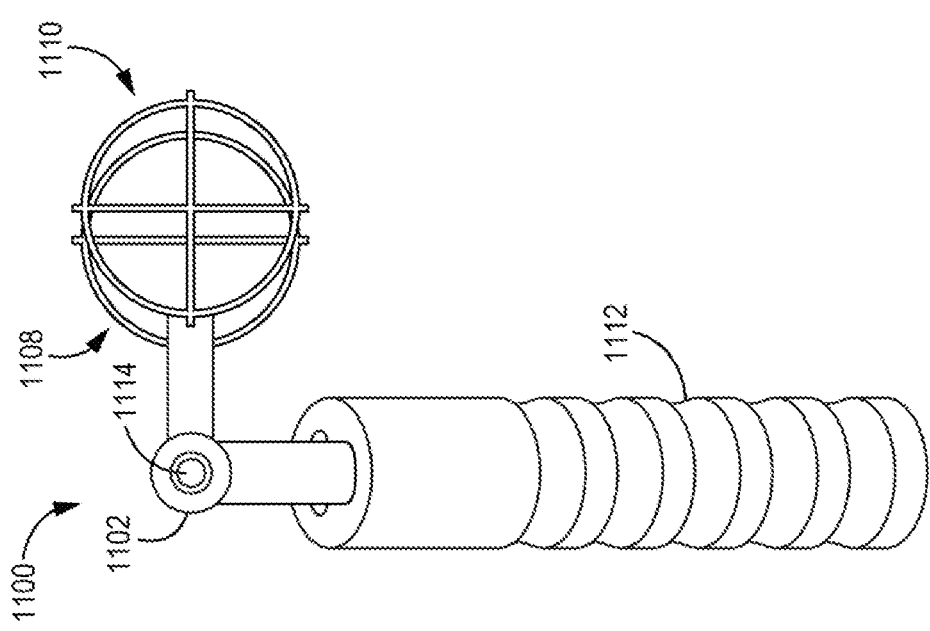

FIGS. 11A-11C illustrate various views of one example of a physical targeting tool, in accordance with one or more techniques of this disclosure. As shown in FIGS. 11A-11C, physical targeting tool 1100 may include main body 1102, first physical sight 1108, second physical sight 1110, and handle 1112.

Main body 1102 may define a channel configured to receive a tool. For instance, main body 1102 may define channel 1114 that is configured to receive a shaft of a rotating tool, such as rotating tool 1004 of FIG. 10. Channel 1114 may have a primary axis that controls movement of a received tool. For instance, where channel 1114 is configured to receive a shaft of a rotating tool, channel 1114 may have a longitudinal axis (e.g., longitudinal axis 1116) about which the shaft may rotate. Channel 1114 may be considered to be configured to receive the tool by being sized such that an inner dimension of channel 1114 is slightly larger than an outer dimension of the tool. For instance, where the tool is a rotating tool, channel 1114 may be cylindrical and have an inner diameter that is slightly larger than an outer diameter of a shaft of the rotating tool. In this way, the shaft of the rotating tool may spin within channel 1114 but may be confined to rotation about longitudinal axis 1116.

Channel 1114 may extend all the way through main body 1102 such that channel 1114 is open at both distal end 1104 and proximal end 1106. Therefore, a rotating tool may be inserted into proximal end 1106, advanced through channel 1114, and come out of distal end 1104.

Physical targeting tool 1100 may include one or more physical targeting features attached to main body 1102. In the example of FIGS. 11A-11C, the physical targeting features include first physical sight 1108 and second physical sight 1110. As shown in FIGS. 11A-11C, first physical sight 1108 and second physical sight 1110 may be displaced along main body 1102 such that first physical sight 1108 and second physical sight 1110 are displaced along longitudinal axis 1116 of channel 1114. Each of first physical sight 1108 and second physical sight 1110 may include a focal point. As shown in FIGS. 11A-11C, first physical sight 1108 may include focal point 1118 and second physical sight 1110 may include focal point 1120. While shown in FIGS. 11A-11C as reticles with crosshairs, each of first physical sight 1108 and second physical sight 1110, and their respective focal points, may be any shape capable of being aligned with displayed virtual guidance (e.g., as displayed by a visualization device, such as visualization device 213 of FIG. 5). Other examples shapes include, but are not limited to, spheres, circles, triangles, and the like. In some examples, both first physical sight 1108 and second physical sight 1110 may be the same shape. In other examples, first physical sight 1108 and second physical sight 1110 may be different shapes.

Focal points 1118 and 1120 may be laterally displaced from channel 1114. For instance, focal point 1118 of first physical sight 1108 may be laterally displaced from longitudinal axis 1116 of channel 1114 by distance $D_1$ and focal point 1120 of second physical sight 1110 may be laterally displaced from longitudinal axis 1116 of channel 1114 by distance $D_2$. In some examples, such as the example of FIGS. 11A-11C, $D_1$ and $D_2$ may be different such axis 1122, which connects focal point 1118 of first physical sight 1108 and focal point 1120 of second physical sight 1110, is not parallel to longitudinal axis 1116 of channel 1114. Where $D_1$ and $D_2$ are different, physical targeting tool 1100 may be considered to have asymmetric sights. In other examples, $D_1$ and $D_2$ may be equal such axis 1122 is parallel to longitudinal axis 1116 of channel 1114. Where $D_1$ and $D_2$ are equal, physical targeting tool 1100 may be considered to have symmetric sights.

Both symmetric and asymmetric cases present various advantages. For instance, physical targeting tools with asymmetric sights may enable a surgeon to maintain a gaze closer to a point of contact between a tool being used and a portion of a patient's anatomy on which the tool is being used.

In some examples, physical targeting tool 1100 may include at least two of the physical targeting features. As discussed herein, during use, a surgeon may attempt to align virtual guidance with the physical targeting features. If only a single physical targeting feature were used, the directionality of the tool guided by physical targeting tool 1100 may not be certain. For instance, if only a single physical targeting feature at a particular position along longitudinal axis 1116 is aligned with corresponding virtual guidance, that particular point may be correctly positioned but the remainder of points may or may not be correctly positioned (i.e., as it takes two different points to define a line).

Handle 1112 may be attached to main body 1102 and be configured to be gripped by a hand of an operator of the tool that channel 1114 is configured to receive. For instance, where the tool is a rotating tool connected to a driver, handle 1112 may be configured to be gripped by a first hand of a surgeon while a second hand of the surgeon operates the driver. By gripping handle 1112 while a rotating tool is actively rotating within channel 1114, the surgeon may prevent rotation of main body 1102 that would otherwise occur. Handle 1112 may be mounted to main body 1102 at an angle (e.g., relative to longitudinal axis 1116) desirable for proper gripping of handle 1112 while a tool within channel 1114 is being operated.

In some examples, physical targeting tool 1100 may be ambidextrous such that physical targeting tool 1100 can be similarly operated by right-handed and left-handed surgeons. In other examples, physical targeting tool 1100 may be not be ambidextrous (i.e., physical targeting tool 1100 may come in "righty" or "leftie" configurations). Where physical targeting tool 1100 is not ambidextrous, handle 1112 of physical targeting tool 1100 may be configured to be gripped by a non-dominant hand of the surgeon. In the example of FIGS. 11A-11C where handle 1112 is located on the left when looking down first physical sight 1108 and second physical sight 1110, handle 1112 may be considered to be configured to be gripped by a left hand.

Physical targeting tool 1100 may be made from any suitable material, or combination of materials. In some examples, physical targeting tool 1100 may be unitarily constructed such that it is one continuous piece. For instance, physical targeting tool 1100 may be 3D printed as a single part. In some examples, physical targeting tool 1100 may be constructed from multiple parts.

In some examples, as opposed to utilizing a separate physical targeting tool, one or more of the physical targeting features may be integrated onto a tool or a driver of the tool. For instance, first physical sight 1108 and/or second physical sight 1110 may be attached to driver 1002.

Figure 12A:
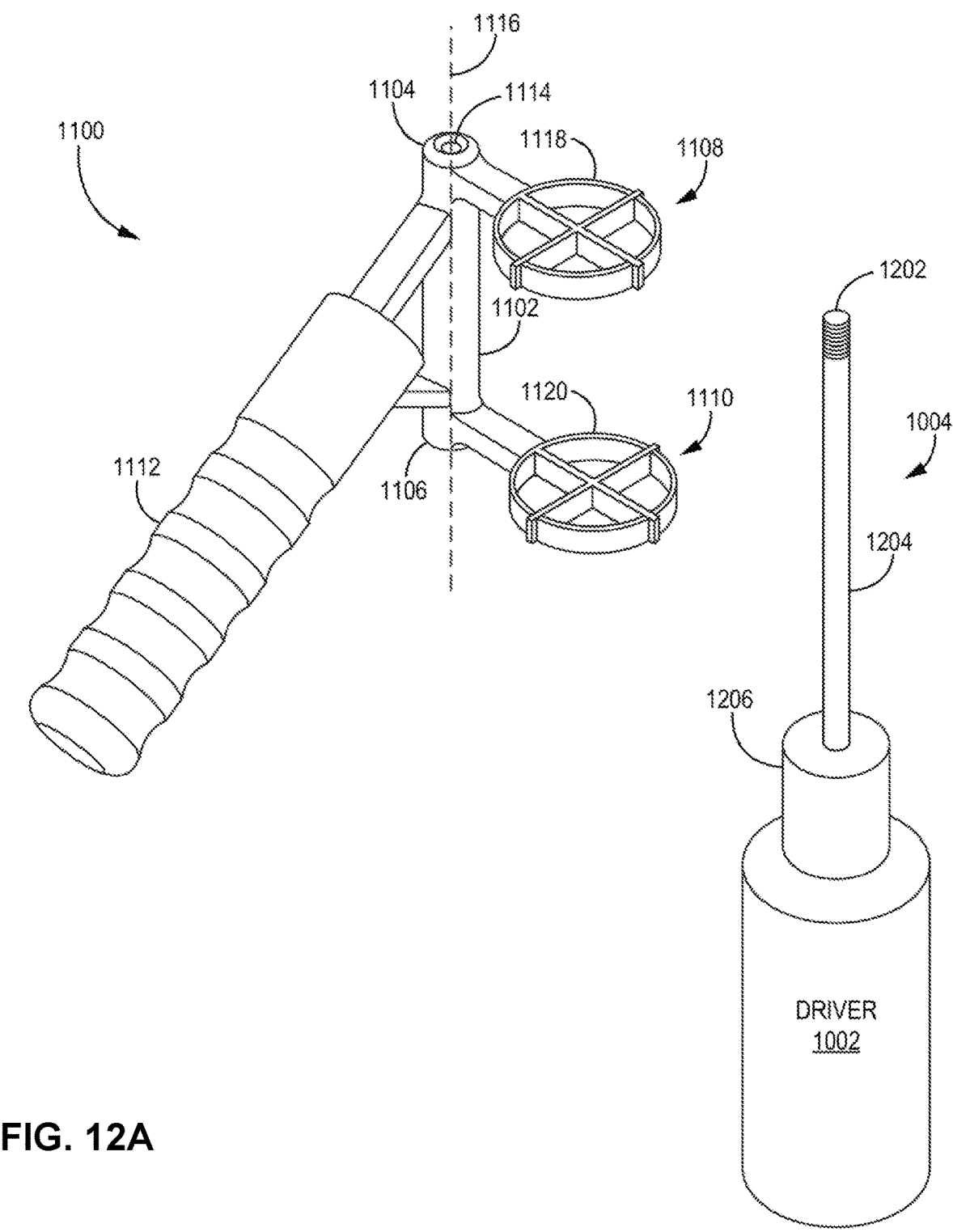
FIGS. 12A and 12B are conceptual diagrams illustrating an example physical targeting tool being attached to a tool, in accordance with one or more techniques of this disclosure.
Figure 12B:
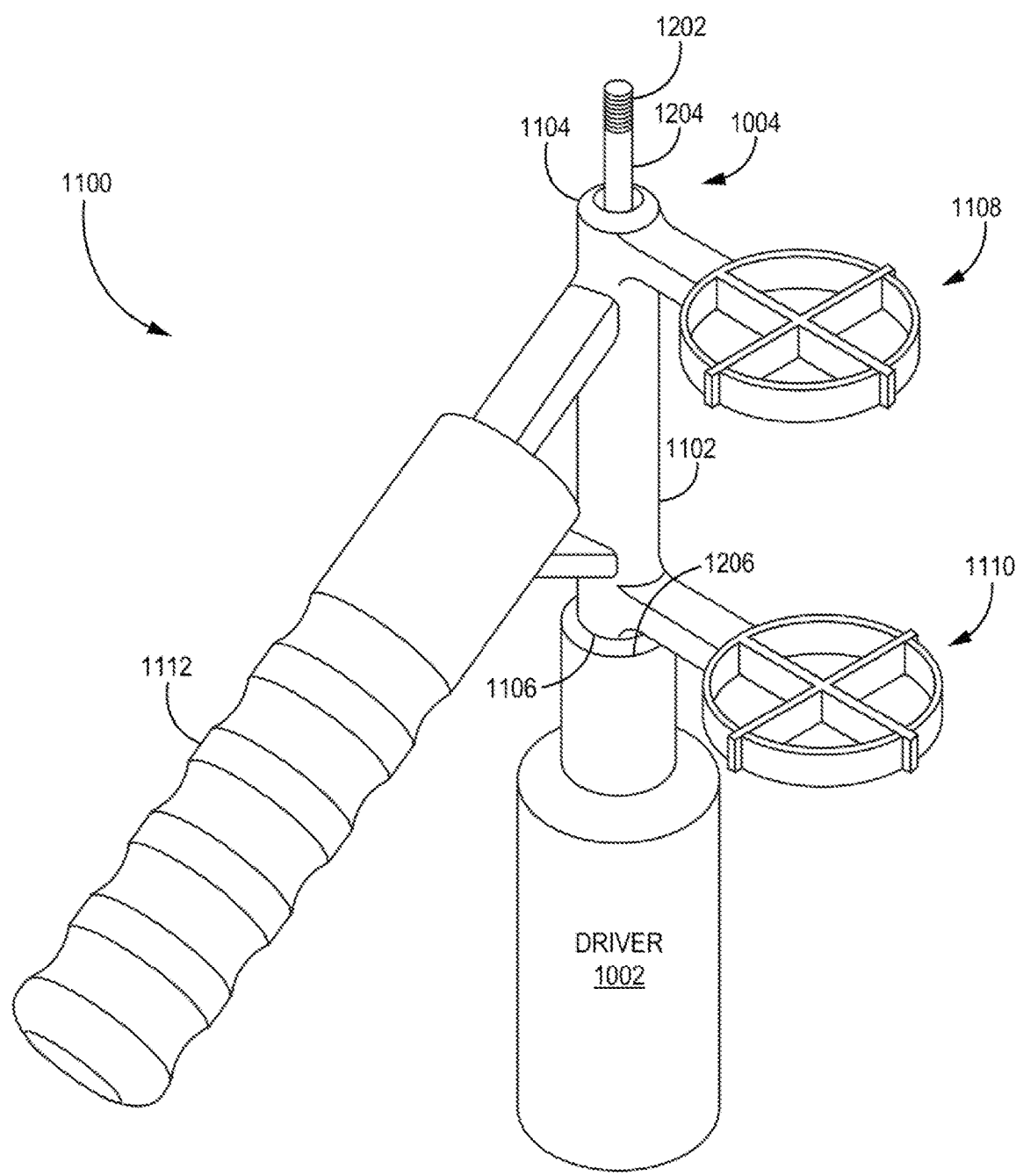

FIGS. 12A and 12B are conceptual diagrams illustrating an example physical targeting tool being attached to a tool, in accordance with one or more techniques of this disclosure. As shown in FIG. 12A, rotating tool 1004 includes distal end 1202, proximal end 1206, and shaft 1204. In the example of FIG. 12A, rotating tool 1004 is a self-tapping guide pin as distal end 1202 is configured to drill and secure rotating tool 1004 in an object (e.g., a patient's bone). Other examples of rotating tools include, but are not limited to, guide pins (e.g., self-tapping guide pins, such as guide 3500), reaming tools, drill bits, and screw drivers. As shown in FIG. 12A, proximal end 1206 may be attached to driver 1002 (e.g., via a chuck or some other mechanical linkage), which may provide rotational power to rotating tool 1004. Examples of driver 1002 include, but are not limited to, drills, surgical motors, and the like. Driver 1002 may be electrically powered, pneumatically powered, or manually powered.

In operation, a surgeon may insert rotating tool 1004 into channel 1114 of physical targeting tool 1100. For instance, the surgeon may insert distal end 1202 of rotating tool 1004 into proximal end 1106 of channel 1114 and advance distal end 1202 through channel 1114 toward distal end 1104 of channel 1114 such that distal end 1202 of rotating tool 1004 emerges from distal end 1104 of channel 1114. While described as rotating tool 1004 being inserted into physical targeting tool 1100, it is noted that a similar outcome may be achieved by sliding physical targeting tool 1100 down rotating tool 1004.

In some examples, the surgeon may continue to advance rotating tool 1004 until proximal end 1106 of channel 1114 comes into contact with driver 1002. In such examples, the surgeon may perform a surgical step using rotating tool 1004 while proximal end 1106 of channel 1114 remains in contact with driver 1002. In other examples, the surgeon may perform a surgical step using rotating tool 1004 while distal end 1104 of channel 1114 remains in contact with anatomy on which rotating tool 1004 is being used.

Figure 13:
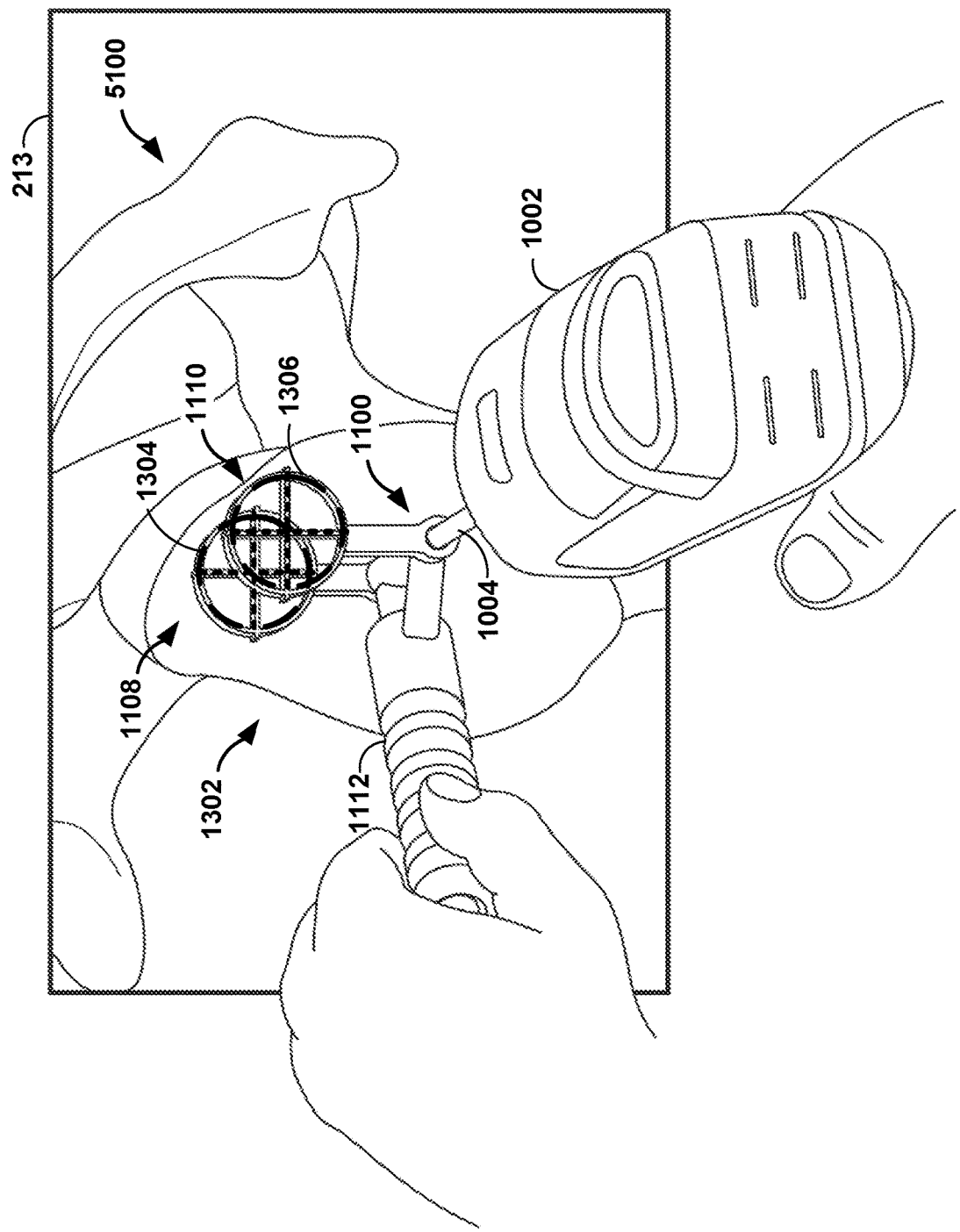
FIG. 13 is a conceptual diagram of virtual guidance that may be provided by an MR system to guide a surgeon performing a surgical step using a physical targeting tool, in accordance with one or more techniques of this disclosure.

FIG. 13 is a conceptual diagram of virtual guidance that may be provided by an MR system to guide a surgeon performing a surgical step using a physical targeting tool, in accordance with one or more techniques of this disclosure. As shown in FIG. 13, the surgeon may bring the combined assembly of driver 1002, rotating tool 1004, and physical targeting tool 1100 into a position near a current surgical step to be performed. In the example of FIG. 13, the current surgical step is installing a guide pin in scapula 5100. However, the techniques of this disclosure are equally applicable to other steps of surgical procedures.

As discussed above, in some examples, a tool, or a driver of a tool, being used to perform a step may obscure or otherwise interfere with a portion of virtual guidance being presented by visualization device 213 to assist with operation of the tool. In accordance with one or more techniques of this disclosure, MR system 212 may display virtual guidance 1302 that guides performance of a surgical step with the use of a physical targeting tool that attaches to a tool. Virtual guidance 1302 may enable the surgeon to achieve correct performance of the surgical step by aligning portions of the one or more physical targeting features of physical targeting tool 1100 with the displayed virtual guidance 1302. Virtual guidance 1302 may be in the form of shapes that correspond to the shapes of the physical targeting features of physical targeting tool 1100. For instance, in the example of FIG. 13 where the physical targeting features include first physical sight 1108 and second physical sight 1110, both in the shape of reticles, virtual guidance 1302 may be in the form of virtually displayed reticles 1304 and 1306, which may be referred to as virtual guidance elements.

As first physical sight 1108 and second physical sight 1110 are offset from channel 1114 of rotating tool 1004, first physical sight 1108 and second physical sight 1110 may not be obscured by driver 1002 during operation of rotating tool 1004. In other words, first physical sight 1108 and second physical sight 1110 may remain visible to the surgeon while the surgeon is operating rotating tool 1004 (e.g., causing driver 1002 to apply rotational force to rotating tool 1004). As such, the surgeon may be able to align, and maintain alignment of, reticles 1304 and 1306 of virtual guidance 1302 with first physical sight 1108 and second physical sight 1110 while the surgeon is operating rotating tool 1004. In other words, MR system 212 may display virtual guidance to be aligned with physical targeting features of the physical targeting tool without the virtual guidance being obscured. In this way, the techniques of this disclosure enable a surgeon to utilize tools, and associated drivers, to perform surgical steps with the assistance of virtual guidance.

While illustrated in the example of FIG. 13 as shapes that correspond to the shapes of the physical targeting features of physical targeting tool 1100, MR system 212 may display the virtual guidance in any manner that enables the surgeon to align physical targeting features of a physical targeting tool with the virtual guidance. Other examples of virtual guidance that MR system 212 may display include, but are not limited to, axes (e.g., an axis connecting focal points of the physical targeting features), points, circles, rings, polygons, planes, X shapes, crosses, or any other shape or combination of shapes.

In some examples, MR system 212 may display the virtual guidance at a same depth as the physical targeting features. For instance, MR system 212 may display reticles 1304 and 1306 of virtual guidance 1302 at the same depths (e.g., positions along the longitudinal axis) as first physical sight 1108 and second physical sight 1110. In some examples, MR system 212 may display the virtual guidance at a different depth than the physical targeting features. For instance, MR system 212 may display reticles 1304 and 1306 of virtual guidance 1302 at positions displaced along the longitudinal axis (e.g., by 10 cm, 20 cm, 50 cm, etc.) from first physical sight 1108 and second physical sight 1110. In either case, the surgeon may be considered to have aligned the physical targeting features with the virtual guidance where the physical targeting features and the virtual guidance at least align in dimensions (e.g., in x and y dimensions, where the z dimension extends along the longitudinal axis).

Figure 14:
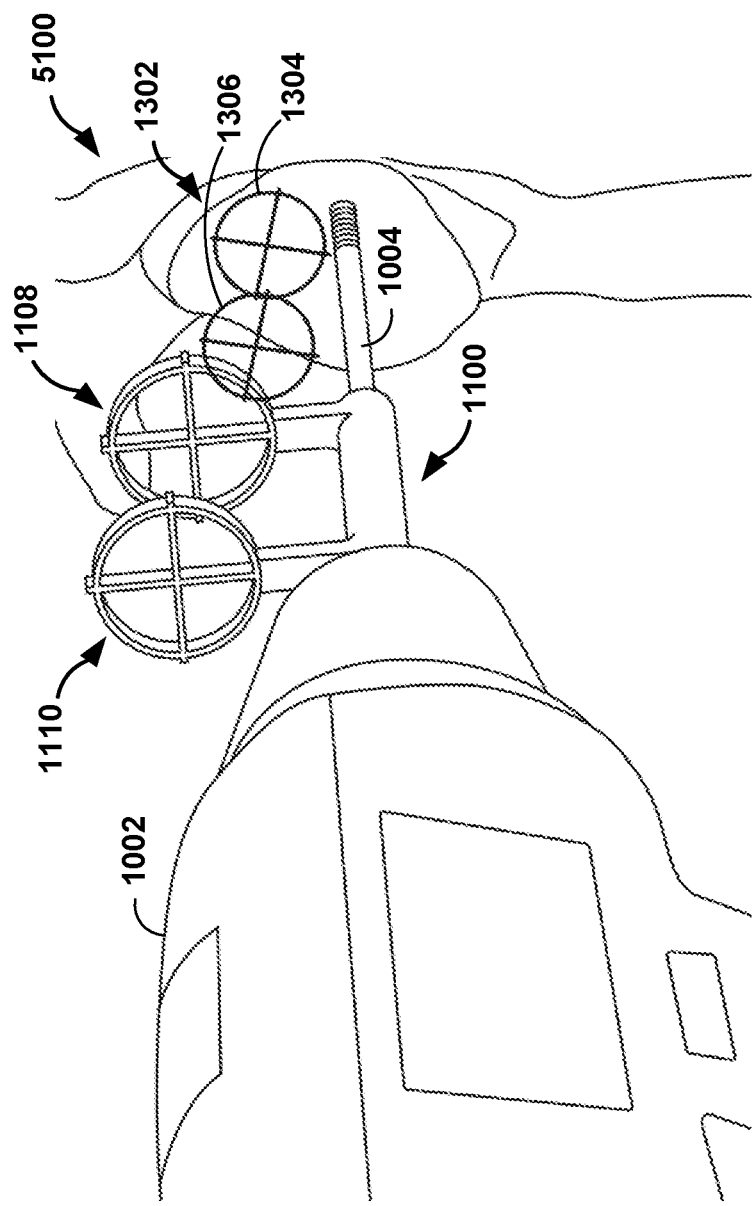
FIG. 14 is a conceptual diagram of virtual guidance that may be provided by an MR system to guide a surgeon performing a surgical step using a physical targeting tool, in accordance with one or more techniques of this disclosure.

FIG. 14 is a conceptual diagram of virtual guidance that may be provided by an MR system to guide a surgeon performing a surgical step using a physical targeting tool, in accordance with one or more techniques of this disclosure. FIG. 14 illustrates a similar scenario as FIG. 13 from a slightly offset perspective. In the example of FIG. 14, first physical sight 1108 and second physical sight 1110 may not yet be aligned with virtual guidance 1302 (e.g., reticles 1304 and 1306). As discussed above, to achieve correct performance of the surgical step, the surgeon may align portions of the one or more physical targeting features of physical targeting tool 1100 with the displayed virtual guidance 1302. In this case, the surgeon may align portions of the one or more physical targeting features of physical targeting tool 1100 with the displayed virtual guidance 1302 by rotating physical targeting tool 1100 clockwise about the axis of rotating tool 1004.

Figure 15:
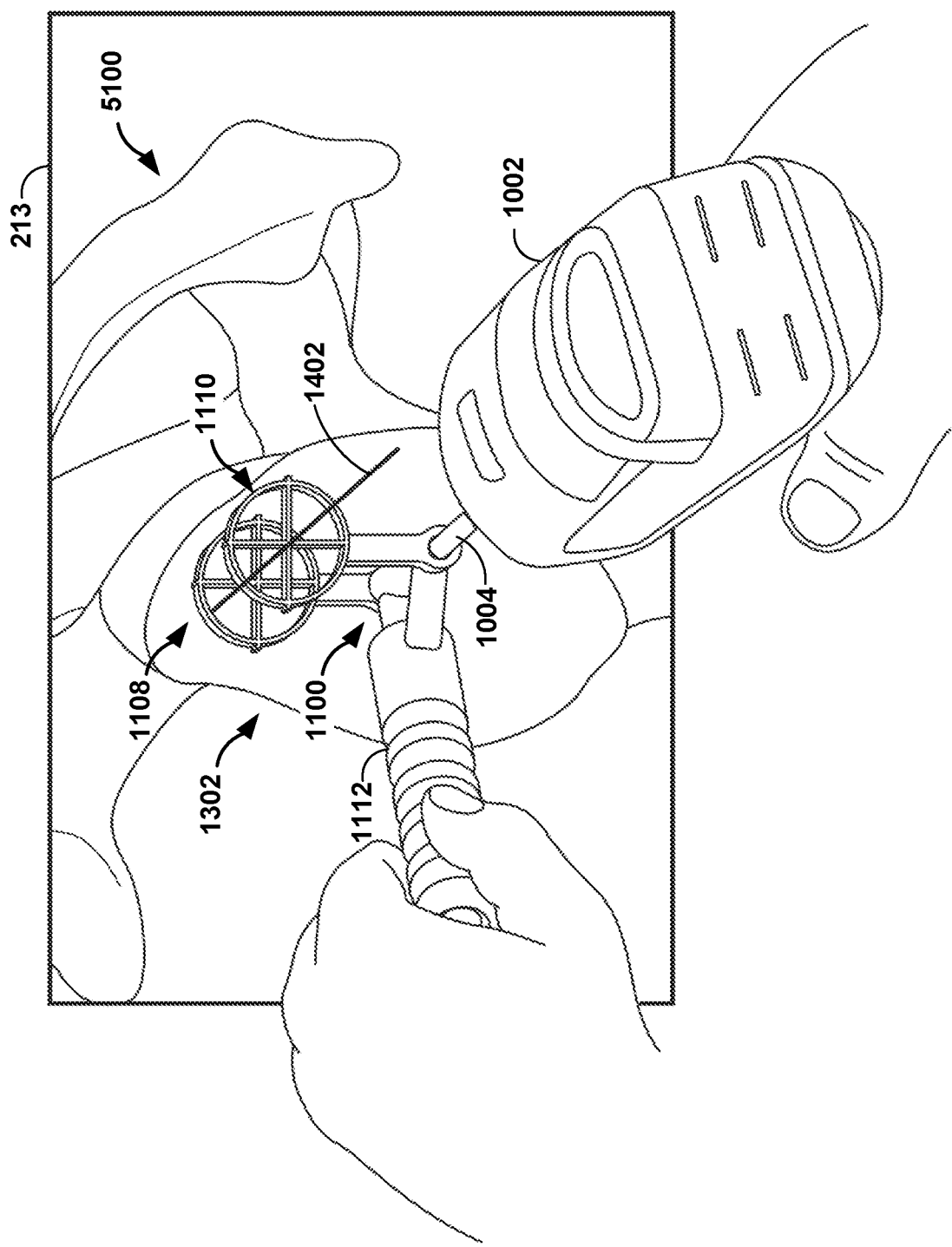
FIG. 15 is a conceptual diagram of virtual guidance that may be provided by an MR system to guide a surgeon performing a surgical step using a physical targeting tool, in accordance with one or more techniques of this disclosure.

For instance, as shown in the example of FIG. 15, MR system 212 may display virtual guidance 1302 as including offset virtual axis 1402. In the example of FIG. 15, a surgeon may enable the surgeon to achieve correct performance of the surgical step by focal points 1118 and 1120 with offset virtual axis 1402. Where targeting tool 1100 has symmetric sights, offset virtual axis 1402 may be parallel to virtual axis 902, through virtual axis 902 may or may not be contemporaneously displayed with virtual guidance 1302.

Figure 16:
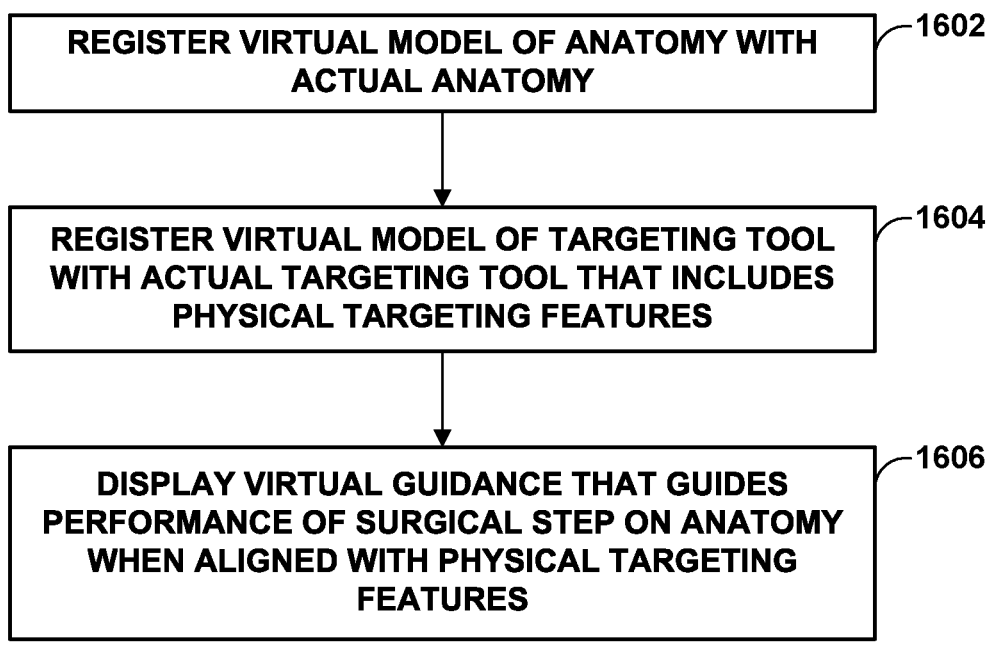
FIG. 16 is a flowchart illustrating example techniques for providing virtual guidance to guide a surgeon performing a surgical step using a physical targeting tool, in accordance with one or more techniques of this disclosure.

FIG. 16 is a flowchart illustrating example techniques for providing virtual guidance to guide a surgeon performing a surgical step using a physical targeting tool, in accordance with one or more techniques of this disclosure. For purposes of explanation, the techniques of FIG. 16 are described as being performed by MR system 212 of FIG. 1. However, other mixed-reality systems may perform the techniques of FIG. 16.

MR system 212 may perform a registration process that registers a virtual bone object with a corresponding bone of the patient (1602) in the field of view presented to the surgeon by visualization device 213. For instance, MR system 212 may obtain a virtual glenoid object (e.g., a virtual model of a portion of an anatomy of the patient) from storage system 206 of FIG. 2. The virtual glenoid object may be generated based on pre-operative imaging (e.g., CT imaging) of the patient's scapula/glenoid. MR system 212 may perform the registration using any suitable process. The registration may produce a transformation matrix between the virtual bone object with the patient's actual bone.

In some examples, MR system 212 may perform a registration process that registers at least a portion of a virtual representation of a physical targeting tool object with a corresponding portion of a physical targeting tool (1604) in the field of view presented to the surgeon by visualization device 213. For instance, MR system 212 may obtain a virtual targeting tool object (e.g., a virtual model of a physical targeting tool, such as physical targeting tool 1100 of FIGS. 11A-11C) from storage system 206 of FIG. 2. The virtual targeting tool object may be obtained from a manufacturer of the physical targeting tool. As one example, the virtual targeting tool object may be a CAD model or other virtual representation of the physical targeting tool. As discussed above, the physical targeting tool may include two or more physical targeting features. In some examples, the virtual targeting tool object may be a representation of an entire targeting tool. For instance, the virtual targeting tool object may be a CAD model or other virtual representation of physical targeting tool 1100. In some examples, the virtual targeting tool object may be a representation of a portion (e.g., a physical targeting feature, handle, etc.) of a targeting tool. For instance, the virtual targeting tool object may be a CAD model or other virtual representation of physical targeting features of the physical targeting tool (e.g., first physical sight 1108 and second physical sight 1110 of physical targeting tool 1100).

As part of the registration(s), MR system 212 may map positions of the virtual representation of the targeting tool object and positions of the virtual bone object into a common coordinate system. As the positions of the virtual representation of the targeting tool object and the virtual bone object correspond to positions of the physical targeting tool object and the patient's actual bone, points on the virtual representation of the targeting tool object and the virtual bone object may correspond to actual positions on the physical targeting tool object and the patient's actual bone. In other words, the positions of the virtual representation of the targeting tool object and the virtual bone object may function as proxies for the positions of the physical targeting tool and the actual bone.

MR system 212 may display virtual guidance that guides performing the surgical step on the anatomy when the physical targeting features of the physical targeting tool are aligned with the displayed virtual guidance (1606). For instance, visualization device 213 of MR system 212 may display virtual guidance 1302 of FIG. 13 or 14. As discussed above, virtual guidance 1302 may be in the form of shapes that correspond to the shapes of the physical targeting features of the physical targeting tool. For instance, visualization device 213 may display first virtual guidance with a shape that corresponds to a shape of a first physical targeting feature of the physical targeting tool, and display second virtual guidance with a shape that corresponds to a shape of a second physical targeting feature of the physical targeting tool (e.g., display reticles 1304 and 1306 of virtual guidance 1302 of FIG. 13 that have shapes corresponding to first physical sight 1108 and second physical sight 1110 of physical targeting tool 1100).

MR system 212 may display the virtual guidance at a position/orientation relative to the virtual bone object. For instance, where the virtual guidance includes an offset virtual axis (e.g., offset virtual axis 1402 of FIG. 15), MR system 212 may obtain (e.g., from a virtual surgical plan) parameters for a current surgical step to be performed. The parameters may specify a location on the virtual bone object at which the step is to be performed and/or an orientation relative to the virtual bone object at which the step is to be performed. For instance, where the step is performed along an axis, the parameters may specify the location as coordinates of a point that the axis passes through (e.g., an x,y,z coordinate set) and the orientation as angles that define the axis (e.g., a polar angle and an azimuth angle). Based on the obtained parameters and dimensions of the physical targeting tool (e.g., $D_1$ and $D_2$ of FIG. 11C), MR system 212 may determine parameters of the offset virtual axis. For instance, where the physical targeting tool has symmetric sights (e.g., where $D_1$ and $D_2$ are equal), MR system 212 may determine the parameters of the offset virtual axis by adding the lateral displacement distance of the physical targeting features to a coordinate of the axis defined by the parameters (e.g., to a coordinate of a plane orthogonal to the axis).

The displayed virtual guidance may enable the surgeon to achieve correct performance of the surgical step by aligning the physical targeting features of the physical targeting tool with the displayed virtual guidance. For instance, the surgeon may align first physical sight 1108 and second physical sight 1110 of physical targeting tool 1100 with reticles 1304 and 1306 of virtual guidance 1302 of FIG. 13. When the physical targeting features of the physical targeting tool with the displayed virtual guidance, the surgeon may activate a driver of a tool physically guided by the physical targeting tool (e.g., activate driver 1002 of rotating tool 1004) and perform the surgical step. As discussed above, the virtual guidance is displayed at a position/orientation, based on the physical targeting tool, relative to an axis for a current surgical step and relative to the virtual bone object. As the virtual bone object is a proxy for the patient's actual bone, this results in the virtual guidance being displayed at a position/orientation relative to the patient's actual bone. Furthermore, as the physical targeting tool controls the position/orientation of the tool being used to perform the surgical step, aligning the physical targeting features of the physical targeting tool with the displayed virtual guidance results in the tool being placed at the desired position/orientation relative to the patient's actual bone.

In some examples, MR system 212 may output an indication of whether the surgeon has aligned the physical targeting features of the physical targeting tool with the displayed virtual guidance. For instance, MR system 212 may output a haptic, audio, graphical, textual, or any other indication perceptible to the surgeon to indicate that the surgeon has aligned the physical targeting features of the physical targeting tool with the displayed virtual guidance.

In some examples, MR system 212 may positively control operation of surgical tools (e.g., driver 1002) based on whether the surgeon has aligned the physical targeting features of the physical targeting tool with the displayed virtual guidance. For instance, if the surgeon has aligned the physical targeting features of the physical targeting tool with the displayed virtual guidance, MR system 212 may enable operation of driver 1002. Similarly, if the surgeon has not aligned the physical targeting features of the physical targeting tool with the displayed virtual guidance, MR system 212 may disable operation of driver 1002.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. A method comprising:
   registering, by one or more processors, a first virtual model of a portion of an anatomy of a patient to a corresponding portion of the anatomy, the first virtual model obtained from a virtual surgical plan;
   registering, by the one or more processors, a second virtual model of a portion of a physical targeting tool to a corresponding portion of the physical targeting tool, wherein:
   the physical targeting tool further comprises a first physical targeting feature, a second physical targeting feature, and a main body,
   the first physical targeting feature and the second physical targeting feature are attached to the main body, and
   the main body defines a channel configured to receive a shaft, the channel having a longitudinal axis, the first physical targeting feature and the second physical targeting feature being displaced along the longitudinal axis of the channel; and
   displaying, by the one or more processors, via a mixed reality (MR) visualization device, virtual guidance that guides performing work on the anatomy, wherein the virtual guidance comprises a first virtual guidance element and a second virtual guidance element, the first virtual guidance element having a first shape that corresponds to a shape of the first physical targeting feature, and the second virtual guidance element having a shape that corresponds to a shape of the second physical targeting feature.

2. The method of claim 1, wherein the first physical targeting feature and the second physical targeting feature each comprises a physical sight.

3. The method of claim 2, wherein each of the first physical targeting feature and the second physical targeting feature comprises a reticle.

4. The method of claim 1, wherein the physical targeting tool is unitarily constructed.

5. The method of claim 1, wherein the channel is open at a proximal end and a distal end such that, when the shaft is inserted into the channel, the shaft passes through both the proximal end and the distal end.

6. The method of claim 1, wherein a distal end of the channel is configured to contact the anatomy of the patient.

7. The method of claim 1, further comprising:
outputting, by the one or more processors, via the MR visualization device, an indication of whether the first physical targeting feature and the second physical targeting feature are aligned with the virtual guidance.

8. The method of claim 7, wherein outputting the indication comprises outputting, by the MR visualization device, at least one of a haptic indication, an audio indication, a graphical indication, or a textual indication perceptible to a user to indicate that the user has aligned the first physical targeting feature and the second physical targeting feature with the first virtual guidance element and the second virtual guidance element, respectively.

9. The method of claim 1, wherein:
the shaft is a shaft of a rotating tool, and
the physical targeting tool further comprises a handle configured to be gripped by a first hand of a user of the rotating tool while a second hand of the user operates a driver of the rotating tool.

10. The method of claim 9, wherein a proximal end of the channel is configured to contact the driver of the rotating tool.

11. The method of claim 9, wherein the shaft is a shaft of a self-tapping guide pin.

12. The method of claim 9, wherein the shaft is a shaft of a screw.

13. The method of claim 9, wherein the shaft is a shaft of a drill bit.

14. The method of claim 1, further comprising controlling, by the one or more processors, operation of a surgical tool based on whether a user has aligned the first physical targeting feature and the second physical targeting feature with the first virtual guidance element and the second virtual guidance element, respectively.

15. The method of claim 1, wherein:
the first physical targeting feature includes a first focal point, and the second physical targeting feature includes a second focal point, and
the method further comprises:
obtaining, by the one or more processors, first parameters that specify at least one of: a location on the first virtual model at which a step of a surgery is to be performed, or an orientation relative to the first virtual model at which the step of the surgery is to be performed;
obtaining, by the one or more processors, second parameters that specify dimensions of the physical targeting tool;
determining, by the one or more processors, based on the first parameters and the second parameters, parameters of an offset virtual axis; and
displaying, by the one or more processors, via the MR visualization device, the offset virtual axis, wherein correct performance of the step is achieved by aligning the first focal point and the second focal point with the offset virtual axis.

16. The method of claim 15, wherein a distance between the first focal point and the longitudinal axis of the channel is greater than a distance between the second focal point and the longitudinal axis of the channel.

17. The method of claim 16, wherein an axis connecting the first focal point and the second focal point is not parallel to the longitudinal axis of the channel.

18. The method of claim 15, wherein a distance between the first focal point and the longitudinal axis of the channel is equal to a distance between the second focal point and the longitudinal axis of the channel.

19. The method of claim 18, wherein an axis connecting the first focal point and the second focal point is parallel to the longitudinal axis of the channel.

* * * * *